(12) United States Patent
Yang et al.

(10) Patent No.: US 6,624,141 B1
(45) Date of Patent: Sep. 23, 2003

(54) PROTAMINE FRAGMENT COMPOSITIONS AND METHODS OF USE

(75) Inventors: Victor C. Yang, Ann Arbor, MI (US); Youngro Byun, Kwangsan-Ku Kwangju (KR)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 09/700,967

(22) PCT Filed: Mar. 9, 1999

(86) PCT No.: PCT/US00/06876

§ 371 (c)(1),
(2), (4) Date: Nov. 16, 2000

(87) PCT Pub. No.: WO00/55196

PCT Pub. Date: Sep. 21, 2000

Related U.S. Application Data

(60) Provisional application No. 60/124,873, filed on Mar. 17, 1999.

(51) Int. Cl.⁷ .............................................. A01N 37/18
(52) U.S. Cl. ................................ 514/2; 514/2; 530/350
(58) Field of Search ................................ 530/350; 514/2

(56) References Cited

U.S. PATENT DOCUMENTS

| | | | |
|---|---|---|---|
| 3,758,683 A | 9/1973 | Jackson | 424/178 |
| 5,747,642 A | 5/1998 | De Felippis | 530/304 |

FOREIGN PATENT DOCUMENTS

| | | | |
|---|---|---|---|
| GB | 1033737 | * | 6/1966 |
| WO | WO 96 35444 | | 11/1996 |

OTHER PUBLICATIONS

Ando and Watanabe, "A New Method for Fractionation of Protamines and the Amino Acid Sequences of Salmine and Three Components of Iridine," *Int. J. Protein Research I*, 221–224, 1969.

Byun et al., "Low Molecular Weight Protamine: A Potential Nontoxic Heparin Antagonist," *Thombosis Research*, 94(1):53–61, 1999; Biosis Abstract.

Cardin and Weintraub, "Molecular Modeling of Protein–Glysosaminoglycan Interactions," *Arteriosclerosis*, 9:21–32, 1989.

Hemostasis and Thrombosis, In: *Pharmacology*, Rang HP, Dale MM, Ritter JM, Gardner P, eds, pp 331–350, Churchill Livingstone Inc., New York, 1995.

Patent Abstracts of Japan, 1998:08; Jun. 30, 1998, referencing Japanese Patent Abstract 10 075777.

Pirhonen et al., "Primary Structures of Two Protamine 2 Variants ST2A and ST2B from Stallion Spermatozoa,"*Biochim. Biophys. Acta*, 1039(2):177–180, 1990, Biosis Abstract.

Smith and Kanuer, "A Heparin Binding Site in Antithrombin III," *J. Biol. Chem.*, 25:11964–11972, 1987.

Suzuki and Ando, "Studies on protamine XIII: The fraction of clupein Y," *J. Biochem.*, 63:701–708, 1968.

WPI Database, week 1986:09; Jan. 20, 1986, referencing Japanese Patent Abstract 61 012265.

International Search Report for counterpart PCT Application Serial No. PCT/US00/06876, mailed Jul. 24, 2000.

* cited by examiner

*Primary Examiner*—Christopher S. F. Low
*Assistant Examiner*—Hope A. Robinson
(74) *Attorney, Agent, or Firm*—Williams, Morgan and Amerson

(57) ABSTRACT

Provided are bioactive, low-toxicity protamine fragments, compositions, combinations, kits and methods of using these components in a variety of embodiments, including neutralizing heparin and reducing post-operative bleeding. Improved protamine fragment-insulin solutions and methods for treating diabetes are also provided.

89 Claims, 4 Drawing Sheets

PROTAMINE FRAGMENT COMPOSITIONS AND METHODS OF USE

The present application is a nationalization of International Patent Application PCT/US00/06876, filed Mar. 19, 1999, which claims priority to provisional application Serial No. 60/124,873, filed Mar. 17, 1999, the entire specification, claims and figures of which are each incorporated herein by reference without disclaimer.

The U.S. Government owns rights in the present invention pursuant to grant numbers RO1 HL38353 and RO1 HL55461 from the National Institutes of Health.

BACKGROUND OF THE INVENTION

1. Field of the Invention

The present invention relates generally to the fields of protein biochemistry and medicine. More particularly, it concerns bioactive, low-toxicity fragments of protamine, and a number of different uses of such protamine fragment compositions. Provided are protamine fragments, compositions, combinations and kits and various methods and uses of such fragments, e.g., in the neutralization of heparin and for association with a variety of therapeutic proteins, including insulin.

2. Description of Related Art

Heparin has become the clinical anticoagulant drug of choice, and is used universally for: prophylaxis of postoperative thromboembolism, in patients with stroke, during various surgical situations, and particularly in all procedures involving extracorporeal blood circulation (ECBC) (Jaques, 1980; Majerus et al., 1996). Extracorporeal blood circulation is employed in numerous clinical situations such as kidney dialysis, open-heart operations, cardiac catheterizations, blood oxygenation, plasmapheresis, organ transplantation, and the implantation of artificial organs. In the United States alone, approximately 15 million ECBC procedures are performed annually (Ma et al., 1994). Approximately 33 metric tons of heparin, representing 500 million doses, are used worldwide each year (Linhardt, 1991). The production figures obtained from the pharmaceutical industry suggest that clinical use of heparin continues to grow rapidly (Linhardt, 1991).

Heparin consists of a heterogeneous mixture of sulfated glycosaminoglycans with a molecular weight ranging from 3,000 to 40,000 daltons. It is made of a repeating unit of D-glucuronic acid and N-acetyl-D-glucosamine residues (Bourin and Lindahl, 1993). The anticoagulant function of heparin was discovered over 70 years ago (Howell, 1922). Heparin exerts its anticoagulant activity primarily via interaction with antithrombin III (Rosenberg, 1987).

Antithrombin III (ATIII) is a circulating inhibitor of the serine proteases in the coagulation cascade, acting more particularly on thrombin and factor Xa but also on factors IXa, XIa, and XIIa. It possesses an arginine center that binds to the active serine site of thrombin (and also the other coagulation factors) to form a covalent bond (Griffith, 1983). Normally this reaction proceeds rather slowly. Binding of heparin to ATIII, however, induces a conformational change of ATIII, rendering the arginine center more accessible to thrombin interaction, and producing a 1000-fold acceleration of the inhibitory effect (Rosenberg, 1987). The binding of heparin to ATIII involves a unique pentasaccharide sequence containing a 3-O-sulfated glucosamine residue (Choay et al., 1981), and entails interaction between specific lysine residues on ATIII and sulfate and carboxylate groups in heparin (Choay et al., 1981; Rosenberg et al., 1979).

Heparin also acts as a template that helps bring thrombin in close proximity to ATIII. Thrombin then cleaves the reactive site bond of ATIII, to which it becomes covalently bound and is irreversibly inhibited. The released heparin can then act on other ATIII molecules. Heparin, however, does not act as a template for the interaction of antithrombin III and factor Xa (Casu et al., 1981). Thus smaller heparin fragments, such as the low molecular weight heparin possessing the ATIII-binding sequence, are able to inhibit factor Xa but not thrombin (Verstraete, 1990).

Systemic heparinization, however, results in a high incidence of bleeding complications (Hirsh, 1984; Kelton and Hirsh, 1984). Major bleeding occurs in 8% to 33% of patients who receive various forms of heparin therapy (Levin and Hirsh, 1986). Nearly 25% of all patients suffering from acute renal failure are subject to increased bleeding risk during and immediately following dialysis (Swartz and Port, 1979). The incidence of bleeding increase with elderly or diabetic patients, patients with ulcers or other multiple traumata, and patients with current cardiac or vascular surgery.

Aside from hemorrhage, there are also other complications associated with the use of heparin, particularly when the drug is administered over a long period. These added complications include thrombocytopenia, alopecia, arterial embolus, and interference with bone repair and maintenance (Hirchboeck et al., 1954). In fact, heparin has been cited as "the drug responsible for the most deaths in patients who are reasonably healthy" (Porter and Jick, 1977).

Low molecular weight heparin (LMWH) was derived from native heparin in an attempt to abate the induced bleeding risk (Verstraete, 1990; Holmer et al., 1986). It contains the specific pentasaccharide sequence in heparin that is required for ATIII binding, and thus fully retains the antithrombotic effect of heparin through inhibition of factor Xa by ATIII. However, it is of insufficient length to bind thrombin and catalyze the inhibition of thrombin by ATIII. LMWH is more effective than regular heparin in preventing deep vein thrombosis and pulmonary embolism after orthopedic surgery but has similar incidence of bleeding (Jensen and Ens, 1993). In a large randomized study in which a continuous intravenous infusion of heparin was compared with a fixed subcutaneous dose of LMWH in patients with venous thrombosis, the incidence of major bleeding was only marginally lower with LMWH (Hull et al., 1992). Enoxparin (Clexane), Kabi-2165 (Fragmin), CY-216 (Fraxiparine), and Novo LHN-1 (Logiparin) are a few commercial LMWH products approved for clinical use.

A major drawback of LMWH lies in the absence of an appropriate clinical antidote to combat the potential risk of induced bleeding. Neither protamine nor platelet factor 4 (PF4, a naturally occurring protein from platelet that is under extensive investigation as a potential replacement of protamine as the anti-heparin agent (Cook et al., 1992) can fully neutralize the anticoagulant effects of LMWH (Lechner et al., 1995; Ryn-McKenna et al., 1990).

To reduce post-operative bleeding, protamine, a clinical heparin antagonist, is routinely administered after cardiac and vascular surgery to reverse the anticoagulant activity of heparin (Jaques, 1973). Protamine consists of a group of heterogeneous polycationic peptides with an average molecular weight of about 4500 daltons. It is generally obtained from fish (Ando et al., 1973). Nearly 67% of the amino acid composition of protamine is arginine (Ando et al., 1973). The polycationic protamine combines electrostatically with the polyanionic heparin to form a stable complex that is devoid of anticoagulant activity. Each milligram of protamine neutralizes approximately 90 units of heparin derived from bovine lung tissue or 115 units of heparin derived from porcine intestinal mucosa. Protamine, however, cannot completely neutralize the anticoagulant activities of low molecular weight heparins (Lechner et al., 1995; Ryn-McKenna et al., 1990; Harenberg et al., 1985; Diness and Ostergaard, 1986; Wakefield et al., 1994), apparently due to an insufficient binding affinity between protamine and LMWH.

In addition to its function as a heparin antagonist, protamine also finds another major pharmacological application. It prolongs the adsorption of insulin, and is therefore combined with insulin to formulate protamine zinc insulin (PZI) and neutral protamine Hagedorn (NPH) insulin. Such formulations allow insulin-dependent diabetic patients to achieve euglycemia with less frequent insulin injections.

However, despite its nearly universal use in clinical practice, current formulations of protamine are nevertheless toxic. Protamine toxicity ranges from mild hypotension (Katz et al., 1987; Ovrum et al., 1992; Kirklin et al., 1986), to severe systemic vascular collapse requiring prompt intervention (Lowenstein et al., 1983; Just-Viera et al., 1984; Hurby et al., 1995), or idiosyncratic fatal cardiac arrest (Olinger et al., 1980; Cobb and Fung, 1982; Sharath et al., 1985; Neidhart et al., 1992).

The protamine toxicity is mediated by several pathways: (i) non-immunological pathway; (ii) immunoglobulin-mediated pathway; (iii) inhibition of carboxypeptidase N; and (iv) other toxic effects. Anaphylactoid type of reactions produced via the first mechanism, which are manifested by complement activation, thromboxane generation, and histamine release, are more common and less dangerous. Anaphylactic types of responses produced via the second pathway, however, are unpredictable, not preventable, and always life-threatening. More than 100 deaths have been attributed to this type of protamine toxicity (Horrow, 1985; Lindblad, 1989). Thus, protamine compositions without any one or more of these or other toxic effects, and the use of such compositions in place of protamine, would represent a significant advance in the art.

SUMMARY OF THE INVENTION

The present invention overcomes one or more of these and other shortcomings in the art by providing bioactive protamines and compositions, combinations and kits thereof, in which the protamines have reduced immunogenicity, antigenicity and/or toxicity compared to native protamine. Preferably, the bioactive, low-toxicity protamines and compositions thereof are low molecular weight protamines. Various methods and uses of such low molecular weight bioactive protamines, compositions, combinations and kits are also provided, including antagonizing heparin functions to reduce post-operative bleeding and prolonging the adsorption of insulin to treat diabetes.

The invention thus provides purified protamines that are bioactive, that have reduced immunoresponsiveness and/or toxicity compared to native protamine and that preferably have a low molecular weight. The terms "protamine", "protamine species", "protamine polypeptide", "protamine peptide" and "protamine fragment" are generally used interchangeably and, unless otherwise specifically stated, each refer to the unique low molecular weight protamines of the invention. Also, unless otherwise specifically stated, the protamines, compositions, combinations, kits, methods and uses of the invention encompass single, highly purified low molecular weight protamine species and more than one, or a plurality of, low molecular weight protamine species.

In providing purified, bioactive protamine species that have reduced toxicity compared to native protamine, the "reduction in toxicity" includes reductions in toxicity that are mediated by any one or more of several mechanisms, including non-immunological pathways, immunoglobulin-mediated pathways, inhibition of carboxypeptidase N, and other toxic effects. "Reductions in toxicity" thus include reductions in anaphylactoid reactions, complement activation, thromboxane generation and histamine release. Clinically, "reductions in toxicity" include reductions in hypotension, systemic vascular collapse and/or idiosyncratic fatal cardiac arrest.

In providing purified protamine species that are bioactive and have reduced immunoresponsiveness, the term "reduced immunoresponsiveness" includes reduced immunogenicity (reduced ability to induce an immune response in an animal in vivo, including T cell and B cell responses, as well as antibody production) and/or reduced antigenicity (reduced ability to be recognized by anti-protamine antibodies) compared to native protamine.

The various purified, bioactive, low-toxicity protamine species of the invention thus have only about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 9%, about 8%, about 7%, about 6%, about 5%, about 4%, about 3%, about 2%, about 1%, about 0.5%, about 0.1%, about 0.05%, about 0.01%, about 0.005%, about 0.001% or less of the immunoresponsiveness and/or toxicity, including low molecular weight protamine species that have no immunoresponsiveness and/or toxicity, within detection limits, compared to native protamine.

Preferably, the purified, bioactive, low-toxicity protamine species will have substantially reduced immunoresponsiveness and/or toxicity compared to native protamine. The term "substantially reduced immunoresponsiveness and/or toxicity" means that the purified, bioactive, low-toxicity protamine species preferably have only about 50% of the immunoresponsiveness and/or toxicity of native protamine, or more preferably about 30% of the imnmunoresponsiveness and/or toxicity of native protamine, or even more preferably have only about 10% or 5% or less of the immunoresponsiveness and/or toxicity of native protamine. Protamine species with only about 4%, about 3%, about 2%, about 1%, about 0.5%, about 0.1%, about 0.05%, about 0.01%, about 0.005%, about 0.001% and no detectable imnmunoresponsiveness and/or toxicity, compared to native protamine, are naturally included as purified, bioactive, low-toxicity protamines with "substantially reduced immunoresponsiveness and/or toxicity compared to native protamine".

As used herein, the term "native protamine" refers to protamine in the state that it is originally isolated in, that is, protamine that includes intact, high molecular weight species. This will be understood to include presently commercially available protamine preparations, as well as protamine isolated from natural sources, such as sperm heads and/or fertilized eggs.

Unless otherwise specifically stated, the purified, bioactive, low-toxicity protamine, protamines, compositions, combinations, kits, methods and uses of the invention encompass single, highly purified, bioactive, low-toxicity protamine species and more than one, or a plurality of, purified, bioactive, low-toxicity protamine species. The invention therefore includes one, two, three, four, five, six, seven, eight, nine or ten or more, distinct, bioactive, low-toxicity protamine species, as well as populations, sub-populations and pluralities thereof. Preferably, "purified" bioactive, low-toxicity protamines are also low molecular weight protamines, such that "purified" refers to the purification of one or more distinct low molecular weight protamine species "away from high molecular weight species". The single, multiple or pluralities of protamine species of the invention are thus those that have been isolated away from, purified free from, or in certain aspects, isolated substantially away from or purified substantially free from, high molecular weight protamine species.

The purified, low-toxicity, preferably low molecular weight, protamine species of the present invention are "bioactive", that is, they retain sufficient bioactivity for any practical purpose. The terms "bioactive" and "sufficient bioactivity" mean that the low-toxicity protamines of the invention are protamine species that at least maintain or retain one, some, most or all of the biological activities of "native protamine".

The biological activities of native protamine include, but are not limited to, the ability to at least partially bind to and/or neutralize heparin and/or low molecular weight heparin and the ability to associate with, or form a complex with, certain therapeutic proteins or peptides, such as insulin or α-interferon. The ability to bind to and/or neutralize low molecular weight heparin is a preferred property of the purified, bioactive, low-toxicity protamines of the present invention. However, the binding properties are not limited to heparin and, for example, may extend to heparan, heparan sulfate and the like.

In various aspects of the present invention, the bioactive protamines will include at least a first protamine species that has at least about 1%, about 2%, about 3%, about 4%, about 5%, about 10%, about 15%, about 20%, about 25%, about 30%, about 35%, about 40%, about 45%, about 50%, about 60%, about 70%, about 75%, about 80%, about 85%, about 90%, about 95%, about 96%, about 97%, about 98%, about 99% or even up to at least about 100% of the heparin or low molecular weight heparin binding and/or neutralizing capability of native protamine. Thus, the present invention provides at least a first purified protamine species, polypeptide or peptide, preferably a low molecular weight protamine, that retains heparin binding and/or neutralization activity and that has reduced immunoresponsiveness and/or toxicity compared to native protamine.

Preferably, the purified, low-toxicity protamine species maintain or retain significant or substantial bioactivity compared to native protamine. The term "significant or substantial bioactivity" means that the purified protamine species preferably maintain or retain at least about 20% of the bioactivity of native protamine, more preferably at least about 40% of the bioactivity of native protamine, and even more preferably maintain or retain at least about 60% or 80% or more of the bioactivity of native protamine.

In that native protamine does not sufficiently bind low molecular weight heparins and cannot completely neutralize the anticoagulant activities of low molecular weight heparins, the present invention is able to provide protamine species that have "at least" about 100% of the heparin or low molecular weight heparin binding and/or neutralizing capability of native protamine. Thus, the low-toxicity protamine species of the invention extend to species that have "more" low molecular weight heparin binding and/or neutralizing capability than native protamine. These include purified protamine species that have "increased bioactivity" compared to native protamine.

Furthermore, it will be understood that preferred purified low-toxicity protamine species will be those that combine preferable levels of bioactivity and acceptably reduced levels of immunoresponsiveness and/or toxicity. Additionally, these characteristics are related, such that for purified protamine species that have dramatically reduced immunoresponsiveness and/or toxicity, for example 10% or 5% or less of the immunoresponsiveness and/or toxicity of native protamine, less substantial bioactivity, for example even 5% or 10% or so would be preferable in certain aspects of the invention. Likewise, for purified protamine species that have less dramatically reduced immunoresponsiveness and/or toxicity, for example 90% or 80% or so of the immunoresponsiveness and/or toxicity of native protamine, more substantial bioactivity, for example 70% or 80% or so would be more preferable in certain aspects of the invention.

The bioactive protamine, protamines, compositions, combinations, kits, methods and uses of the invention generally comprise at least a first purified low molecular weight bioactive protamine that has a molecular weight of between about 400 and about 3000 daltons or so. In certain aspects of the invention, the at least a first purified low molecular weight bioactive protamine has a molecular weight of between about 400 and about 2500 daltons, about 400 and about 2000 daltons, about 400 and about 1500 daltons, about 400 and about 1400 daltons, about 400 and about 1350 daltons, about 400 and about 1300 daltons, about 400 and about 1200 daltons, about 400 and about 1100 daltons, about 400 and about 1000 daltons. In further aspects, the at least a first purified low molecular weight bioactive protamine has a molecular weight of between about 500 and about 3000 daltons, about 600 and about 3000 daltons, about 700 and about 3000 daltons, about 800 and about 3000 daltons, about 900 and about 3000 daltons, about 1000 and about 3000 daltons, about 1500 and about 3000 daltons. In still further aspects, the at least a first purified low molecular weight bioactive protamine has a molecular weight of between about 2000 and about 3000 daltons, about 500 and about 2500 daltons, about 1000 and about 2000 daltons, or about 1000 and about 1500 daltons.

In certain preferred embodiments, the composition comprises at least a first purified low molecular weight bioactive protamine that has a molecular weight of between about 1100 and about 1350 daltons, preferably of between about 1150 and about 1300 daltons.

In further aspects of the present invention, the protamine, protamines, compositions, combinations, kits, methods and uses of the invention comprises at least a first purified low molecular weight bioactive protamine that has a molecular weight of about 400, about 450, about 500, about 600, about 700, about 800, about 900, about 1000, about 1100, about 1150, about 1200, about 1250, about 1300, about 1350, -about 1400, about 1500, about 1600, about 1700, about 1800, about 1900, about 2000, about 2100, about 2200, about 2300, about 2400, about 2500, about 2600, about 2700, about 2800, about 2900 or about 3000 daltons.

In currently preferred embodiments, the composition comprises at least a first purified low molecular weight bioactive protamine that has a molecular weight of about 1200 daltons. "About 1200 daltons" includes 1160, 1170, 1180, 1190, 1195, 1205, 1210, 1220, 1230, 1240 daltons and such like, Defined aspects of the invention are thus compositions comprising at least a first purified, low-toxicity, bioactive protamine. Such compositions may comprise only a first purified bioactive protamine species, or at least a first and at least a second purified bioactive protamine species. In yet other aspects, these compositions further comprise at least a third, at least a fourth, at least a fifth, at least a sixth, at least a seventh, at least an eighth, at least a ninth or at least a tenth purified bioactive protamine species, polypeptide and/or peptide. In certain embodiments, the composition comprises a population, sub-population or plurality of purified bioactive protamine species, polypeptides and/or peptides that have reduced immunogenicity, antigenicity and/or toxicity compared to native protamine.

The population, sub-population or plurality of low-toxicity protamine species can each have similar, or in other aspects, distinct molecular weights within the above stated ranges. Thus, in certain embodiments, the compositions comprise a plurality of purified bioactive protamine species, polypeptides and/or peptides that have a molecular weight of between about 400 and about 2500 daltons, while in further embodiments, the compositions comprise a plurality of purified bioactive protamine species, polypeptides and/or peptides that have a molecular weight of about 1200 daltons.

Any source of protamine is contemplated for use in the preparation of the instant protamine compositions, combinations, kits, methods and uses. Preferred sources of protamine include, but are not limited to, mammals, amphibians and fish, with salmon and herring being more preferred in certain aspects of the invention. Thus, in particular embodiments, the compositions, combinations, kits, methods and uses comprise at least a first purified bioactive salmine (salmon) protamine and/or at least a first purified bioactive clupeine (herring) protamine.

In certain embodiments of the present invention, the purified, bioactive protamine compositions will further comprise at least a first additional (distinct) biologically active agent. The term "at least a first additional or distinct biologically active agent", as it applies to the compositions, combinations, kits, methods and uses of the invention means at least a first biologically active agent "in addition to" the at least a first purified bioactive protamine species. Accordingly, the at least "a first additional" biologically active agent could well be termed at least "a second, distinct" biologically active agent, with the "at least a first purified bioactive protamine" being at least a first biologically active agent. However, this is purely a matter of semantics, and the practical meaning will be clear to those of ordinary skill in the art.

In exemplary embodiments, the low-toxicity, preferably low molecular weight, bioactive protamine-containing compositions, combinations, kits, methods and uses of the invention will further comprise at least one additional biologically active agent in the form of at least a second coagulant, coagulation factor or coagulative, thrombotic or clot-inducing therapeutic agent. A plurality of coagulants, coagulation factors or coagulative, thrombotic or clot-inducing therapeutic agents may also be employed.

Exemplary coagulation factors for such uses include Tissue Factor and Tissue Factor derivatives, including truncated, mutant, dimeric, polymeric and multimeric Tissue Factor derivatives (WO 96/01653; specifically incorporated herein by reference); one or more of the vitamin K-dependent coagulation factors, preferably Factor II/IIa, Factor VII/VIIa, Factor IX/IXa and/or Factor X/Xa; and other coagulation factors such as Factor V/Va, VIII/VIIIa, Factor XI/XIa, Factor XII/XIIa and Factor XIII/XIIIa. Further suitable coagulation factors are Russell's viper venom Factor X activator; platelet-activating compounds, such as thromboxane $A_2$ and thromboxane $A_2$ synthase; and inhibitors of fibrinolysis, such as α2-antiplasmin.

Further biologically active agents include therapeutic proteins to be delivered to an animal or patient. Preferred therapeutic proteins are generally those that have an acidic $pK_a$ value are preferred for use with the low molecular weight protamine compositions. The biologically active proteins for use in combination with the compositions, combinations, kits, methods and uses of the invention include, but are not limited to, insulin (including recombinant insulin), preferably human insulin, and α-interferon.

The present invention also provides pharmaceutical compositions comprising a biologically effective amount of at least a first purified bioactive protamine that has reduced immunogenicity, antigenicity and/or toxicity compared to native protamine, and a pharmaceutically acceptable diluent, excipient or carrier. Injectable pharmaceutical compositions exemplify the pharmaceuticals of the invention. In other aspects, the pharmaceutical composition further comprises a biologically effective amount of at least a first biologically active agent, such as a coagulant or a protein with an acidic $pK_a$ value.

In certain embodiments, the pharmaceutical composition further comprises a biologically effective amount of insulin, human insulin and/or α-interferon. The invention thus provides pharmaceutical compositions comprising a combined effective amount of at least a first purified bioactive, low-immunoresponsive and/or low-toxicity protamine and insulin, formulated in a pharmaceutically acceptable diluent or vehicle.

Also provided are kits comprising, in at least a first suitable container, a composition comprising one or more purified bioactive, low-immunoresponsive and/or low-toxicity protamines. The kits may also be combination kits comprising, in at least a first suitable container, a composition comprising at least a first purified bioactive, low-immunoresponsive and/or low-toxicity protamine and at least a first biologically active agent, such as a coagulant or a protein with an acidic $pK_a$ value. Biologically effective amounts of insulin, human insulin and/or α-interferon are currently preferred. The protamines and other biologically active agent(s) of the kits may be formulated in a single container or in at least two distinct containers.

Still further kits of the invention are those that comprise at least a first suitable container comprising at least a first anticoagulant; and at least a second suitable container comprising at least a first purified bioactive protamine in accordance with the present invention. Currently preferred anticoagulants for use in such kits are heparin and low molecular weight heparin. These kits may also comprise further biologically active agents, such as additional anticoagulants, additional coagulants, proteins, insulin, α-interferon and the like.

The purified bioactive protamines, compositions, combinations and kits of the invention have uses in binding, and preferably inhibiting and/or inactivating, heparin and/or low molecular weight heparin in vitro and in vivo; have uses as heparin antagonists and/or low molecular weight heparin antagonists in vitro and in vivo; have uses in ameliorating and/or reversing the anticoagulant activity of heparin and/or low molecular weight heparin in vitro and in vivo; and have uses in preventing or reducing pre-, mid- and/or post-operative bleeding, such as when following heparin and/or low molecular weight heparin administration to an animal or human subject.

Where the purified bioactive protamines and compositions of the invention have been combined with biologically active agents, proteins with acidic $pK_a$ values, insulin and/or α-interferon, the resultant compositions and kits of the invention have uses in prolonging the adsorption and/or the bioavailability of the biologically active agents, proteins with acidic pa values, insulin and/or α-interferon upon administration to an animal or human subject. Purified bioactive protamine compositions and kits in combination with insulin are particularly intended for use in treating diabetes in an animal or human subject.

The invention thus further provides for the use of a purified bioactive protamine composition, combination and/or kit in the manufacture of a medicament for use in treating post-operative bleeding in an animal or human subject. The invention still further provides for the use of a purified bioactive protamine-insulin composition or combination, and/or kit, in the manufacture of a medicament for use in treating diabetes in an animal or human subject.

The present invention further provides methods of preparing at least a first bioactive, preferably low molecular weight, protamine or protamine fraction that has reduced immunoresponsiveness and/or toxicity compared to native protamine (or a plurality or population of such protamines or protamine fractions). The methods generally comprise contacting a native protamine composition with at least a first proteolytic composition comprising at least a first proteolytic enzyme in an amount and for a period of time effective to produce a low molecular weight bioactive protamine, protamine fraction or a plurality or population thereof.

The types and amounts of the proteolytic compositions and enzymes, and the times of incubation, exposure or contact, can be used to prepare low molecular weight bioactive protamine species, polypeptides or peptides that have any of the molecular weights referenced herein, as exemplified by those of between about 450 daltons and about 2500 daltons; between about 450 daltons and about 1350 daltons; and of about 1200 daltons or so.

In certain aspects of the invention, the at least a first proteolytic enzyme is removed from the admixture after the low molecular weight bioactive protamine(s) is produced. The methods thus further comprise isolating the at least a first low molecular weight protamine polypeptide thus produced. Accordingly, the invention encompasses the at least a first low molecular weight protamine polypeptide(s) produced. The at least a first low molecular weight bioactive protamine(s) so produced may also be formulated in a pharmaceutically acceptable composition, combination or kit.

Proteolytic enzymes contemplated for use in the production of the low molecular weight bioactive protamine species, polypeptides and/or peptides include, but are not limited to, thermolysin, ficin, collagenase, kallikrein, proline-specific endopeptidase, or any combination thereof. In other embodiments, the methods comprise contacting the native protamine composition with at least a first and at least a second proteolytic enzyme.

The invention further provides methods of selecting an improved low molecular weight protamine polypeptide, species or fraction, comprising selecting from a plurality of low molecular weight protamine polypeptides, species or fractions a low molecular weight protamine polypeptide, species or fraction that substantially retains the bioactivity of native protamine and has substantially reduced immunoresponsiveness and/or toxicity as compared to native protamine.

The methods of selecting an improved low molecular weight protamine polypeptide, species or fraction generally comprise preparing a population of low molecular weight protamine polypeptides, species or fractions and selecting from the population of low molecular weight protamine polypeptides, species or fractions a low molecular weight protamine polypeptide, species or fraction that retains substantial bioactivity and has substantially reduced immunoresponsiveness and/or toxicity compared to native protamine. The population of low molecular weight protamine polypeptides, species or fractions are preferably generated by contacting a native protamine composition with at least a first proteolytic composition comprising at least a first proteolytic enzyme, as described above.

In certain embodiments, the population of low molecular weight protamine polypeptides is first selected for bioactivity, and then for reduced immunoresponsiveness. In other embodiments, the population of low molecular weight protamine polypeptides is first selected for reduced immunoresponsiveness, and then for bioactivity. These properties may be balanced and off-set to yield a range of improved low molecular weight protamines.

In certain aspects of these methods, any proteolytic enzyme is removed after the improved low molecular weight bioactive protamine(s) is identified. The methods thus further comprise isolating the improved low molecular weight protamine polypeptide so identified. Accordingly, the invention encompasses the improved low molecular weight protamine polypeptide(s) identified. The improved low molecular weight bioactive protamine(s) so identified may also be formulated in a pharmaceutically acceptable composition, combination or kit.

Also provided by the present invention are methods of inhibiting or inactivating heparin or low molecular weight heparin, comprising contacting heparin or low molecular weight heparin with an effective amount of at least a first purified, low-toxicity bioactive protamine in accordance with the present invention.

In certain preferred embodiments, the heparin or low molecular weight heparin is located within a mammal and the composition is administered to the mammal. In particular aspects of the invention, the heparin or low molecular weight heparin is contacted with a combined effective amount of the composition comprising at least a first purified bioactive protamine and at least a second, distinct agent, such as a coagulant, a protein with an acidic $pK_a$ value, insulin and/or α-interferon.

The invention further provides methods of ameliorating or reducing an effect of heparin in a mammal, comprising administering to the mammal a therapeutically effective amount of at least a first pharmaceutical composition comprising at least a first purified bioactive protamine that has reduced immunoresponsiveness and/or toxicity compared to native protamine. In certain aspects, the mammal has diabetes and/or is receiving injections of an insulin-protamine complex.

The invention also provides methods of treating or preventing excessive bleeding in a mammal, comprising administering to the mammal a therapeutically effective amount of at least a first pharmaceutical composition comprising at least a first purified bioactive protamine that has reduced immunoresponsiveness and/or toxicity compared to native protamine. In certain aspects, at least a second coagulant or coagulative, thrombotic or clot-inducing therapeutic agent is further administered to the mammal. In certain aspects, the mammal has diabetes and/or is receiving injections of an insulin-protamine complex. The excessive bleeding can be associated with a number of different conditions, including, but not limited to, systemic heparinization, extracorporeal blood circulation, one or more particular diseases or disorders, a trauma or with surgery.

The instant bioactive protamine compositions, combinations and kits also find use in prolonging the bioavailability of various biologically active or therapeutic proteins and/or peptides. Thus, the present invention provides methods of prolonging the bioavailability of a protein with an acidic $pK_a$ value, such as insulin, human insulin or α-interferon upon administration to a mammal, comprising co-administering the protein with an acidic $pK_a$ value, insulin or α-interferon to the mammal in combination with an effective amount of at least a first purified bioactive protamine that has reduced immunoresponsiveness and/or toxicity compared to native protamine.

Also provided by the present invention are methods of treating or preventing diabetes in a mammal, comprising administering to the mammal a therapeutically effective amount of insulin and at least a first purified bioactive protamine that has reduced immunoresponsiveness and/or toxicity compared to native protamine. The insulin and the at least a first purified bioactive protamine may be administered in a single pharmaceutical composition or in distinct pharmaceutical compositions administered within a biologically effective time.

In all uses and methodological aspects of the present invention, the mammals to be treated include human subjects.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
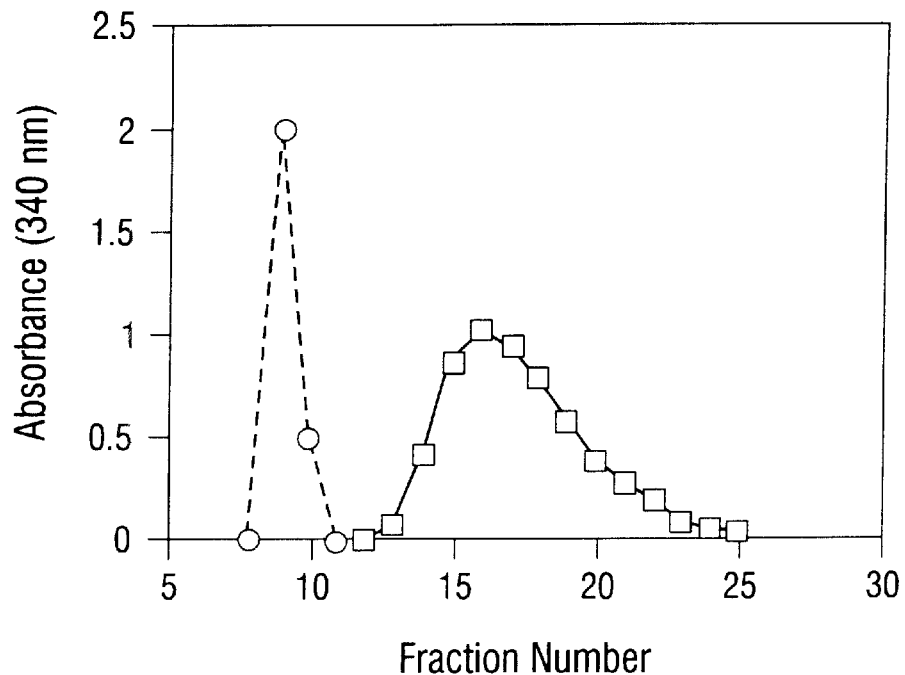
FIG. 1. Elution profile on Sephadex G-25 of protamine (○) and thermolysin-digested protamine (□). Absorbance at 340 nm is shown on the vertical axis, and the fraction number is shown on the horizontal axis.

Extracorporeal blood circulation (ECBC) has become one of the most widely and frequently used medical procedures in recent years. It is employed in clinical situations such as kidney dialysis and cardiopulmonary bypass. In the United States alone, approximately 15 million ECBC procedures have taken place each year. All these applications require heparin anticoagulation to prevent clotting in the devices. Systemic heparinization, however, results in a high incidence of bleeding complications (Hirsh, 1984; Kelton and Hirsh, 1984). In fact, heparin has been cited as "the drug responsible for the most deaths in patients who are reasonably healthy" (Porter and Jick, 1977).

To prevent post-operative bleeding, protamine, a clinical heparin antagonist, is routinely administered after cardiac and vascular surgery to reverse the anticoagulant activity of heparin. Despite its nearly universal use in clinical practice, protamine is nevertheless a toxic compound. Protamine toxicity ranges from mild hypotension to severe, or ultimately fatal cardiac arrest. Indeed, the administration of heparin and protamine has been suggested as the major cause of morbidity and mortality for patients undergoing cardiopulmonary bypass operations (Weiler et al., 1990).

In addition to its function as a heparin antagonist, protamine also prolongs the adsorption of insulin, and is therefore combined with insulin to formulate protamine zinc insulin (PZI) and neutral protamine Hagedorn (NPH) insulin. Such formulations allow insulin-dependent diabetic patients to achieve euglycemia with less frequent insulin injections.

Despite its nearly universal use in clinical practice, protamine is a toxic compound. Protamine toxicity ranges from mild hypotension (Katz et al., 1987; Ovrum et al., 1992; Kirklin et al., 1986), to severe systemic vascular collapse requiring prompt intervention (Lowenstein et al., 1983; Just-Viera et al., 1984; Hurby et al., 1995), or idiosyncratic fatal cardiac arrest (Olinger et al., 1980; Cobb and Fung, 1982; Sharath et al., 1985; Neidhart et al., 1992). Intravenous administration of protamine is often associated with adverse respiratory (e.g., wheezing, bronchospasm, pulmonary edema, hypertension) and cardiovascular (e.g., hypotension, preserved cardiac contractility, systemic vasodilatation, bradycardia, ventricular fibrillation, shock) reactions (Weiler et al., 1990; Jaques, 1973; Levinson and Ohm, 1995; Metz and Horrow, 1994; Weiss and Adkinson, 1991; Horrow, 1988; Lindblad, 1989; Cormack and Levy, 1993).

Recent research also suggests that unbound protamine would affect myocyte contractile processes causing myocardial depressant reactions (Hird et al., 1995; Wakefield et al., 1992), as well as calcium overload in the myocardium. (Park et al., 1994). In addition, protamine is known to possess its own anticoagulant functions (Adkins and Hardy, 1967; Cobel-Geard and Hassouna, 1983), and its use in heparin reversal is at times accompanied by the phenomenon of heparin rebound (Kuitunen et al., 1991; Ellison et al., 1974).

More than 200 reports of adverse reactions to protamine have been documented (Weiler et al., 1990; Levinson and Ohm, 1995; Metz and Horrow, 1994; Weiss and Adkinson, 1991; H1988; Lindblad, 1989; Cormack and Levy, 1993; Horrow, 1985), the majority being published in the last decade. The number of publications that, directly or indirectly, related to protamine-induced reactions during the past five years well exceeds 300. This dramatic increase in literature reports is partly due to an arising recognition of the severity and frequency of protamine-induced complications, and partly to the more wide spread use of protamine resulting from the evolution of coronary artery bypass surgery and cardiac catheterization as common therapeutic and diagnostic modalities.

A survey conducted in 1985 concluded that the most frequently cited profusion accident in cardiopulmonary bypass operations is the "protamine reaction" which is observed by two-thirds of the respondents, and is thought to be more or less responsible for more than 85 patient deaths (Kurusz, 1986). More recent reports indicate that clinically significant systemic arterial hypotension and pulmonary artery hypertension has been noted in 4% of cases and nearly 100 deaths have been attributed to the use of protamine (Levinson and Ohm, 1995; Metz and Horrow, 1994; Weiss and Adkinson, 1991; Lindblad, 1989; Cormack and Levy, 1993).

A recent study estimated the overall incidence of protamine reactions after cardiac surgery was about 11% (Weiler et al., 1990). Realizing that protamine is used in virtually all of the 400,000 cardiac operations performed in this country annually (Levinson and Ohm, 1995), the overall incidence of protamine reactions is significant. These investigators suggested that the combined use of heparin and protamine during cardiopulmonary bypass to control coagulation may be a major cause of morbidity and mortality in patients undergoing such procedures.

The protamine toxicity is mediated by several pathways: (i) non-immunological pathway; (ii) immunoglobulin-mediated pathway; (iii) inhibition of carboxypeptidase N; and (iv) other toxic effects. Anaphylactoid type of reactions produced via the first mechanism, which are manifested by complement activation, thromboxane generation, and histamine release, are more common and less dangerous. Anaphylactic types of responses produced via the second pathway, however, are unpredictable, not preventable, and always life-threatening. More than 100 deaths have been attributed to this type of protamine toxicity (Horrow, 1985; Lindblad, 1989).

Non-immunological-Mediated Pathway

Recent research implicates that a non-immunological pathway via complement activation and eicosanoid generation, particularly thromboxane, may be responsible for many of the acute manifestations observed during protamine reversal of heparin anticoagulation (Morel et al., 1990; Morel et al., 1987; Lowenstein and Zapol, 1990). Because of their relatively long chain lengths and polyionic nature, heparin and protamine form large aggregates both in vitro and in vivo with network-like structures. These large heparin-protamine complexes (HPC), which behave like the antibody-antigen complexes, activate the complement system (Rent et al., 1975).

Activation of the complement cascade results in the generation of anaphylatoxin C3a, C4a, and C5a (Weiler et al., 1990; Click et al., 1989; Conzen et al., 1989), causing an acute profound leukopenia with pulmonary white blood cell sequestration and the release of thromboxane. Thromboxane is a potent vasoconstrictor and its liberation can cause transient but severe pulmonary hypertension and hypoxemia (Morel et al., 1990; Lowenstein and Zapol, 1990; Weiler et al., 1985). Anaphylatoxin C3a is also spasmogenic to smooth muscle, and thus can induce histamine release from mast cells and basophils with subsequent smooth muscle contraction and alterations in vascular permeability (Lowenstein et al., 1983; Weiler et al., 1985). Anaphylatoxin C5a, in addition to the above properties, interacts with receptors on leukocytes to promote chemotaxis and the release of lysosomal enzymes and superoxide. Alternatively, HPC can also introduce a non-cytotoxic, direct degranulation of mast cells, causing the release of vasoactive histamine (Jaques, 1973; Horrow, 1985; Weiler et al., 1985).

Shanberge et al. (1987) indicate that the higher the ratio of protamine to heparin, the larger the size of the HPC, and the more severe the activation of the complement system. Recent clinical studies also suggest that activation of the complement system by HPC requires a critical size for the complex to bind with C1q (Cavarocchi et al., 1985); the prelude of the activation event. The HPC formed with immobilized protamine produced a significantly lower complement consumption than that with free protamine (Yang et al., 1991b; Byun et al., 1996). This is simply because only a single layer of heparin would be able to adsorb on the resin-immobilized protamine, and the HPC thus formed would not be able to reach the critical size required to bind C1q, unlike those large, network-type aggregates formed between heparin and free protamine.

In an attempt to find a protamine substitute that could neutralize heparin without cardiovascular side effects, Wakefield and co-workers (Wakefield et al., 1994; Wakefield et al., 1996) created lysine-containing peptides of similar length to protamine (approximately 32 peptides), but with various variable positive charges. Their studies show that heparin reversal depends on the availability of positive charges on the peptides; approaching that of protamine when the charges approach. The induction of the non-immunological adverse side effects by these peptides, however, is also dependent on the overall charges on the peptides. The greater the net positive charge of the molecule, the more toxic the compound.

Immunological-Mediated Pathway

Patients who have been pre-exposed to protamine may develop anti-protamine antibodies (e.g., IgG, IgE). In the case of true "anaphylactic" response (termed "Type I protamine hypersensitivity"; Weiss and Adkinson, 1991; Horrow, 1988; Lindblad, 1989; Horrow, 1985; Weiler et al., 1985), which is of longer duration and is frequently life-threatening in nature, protamine crosslinks cell surface anti-protamine IgE antibodies on mast cells and basophils, leading to mediator release and systemic vascular dilation and hypotension and/or bronchoconstriction. Right heart failure and hypoxemia precede left heart failure, circulatory collapse and death. Alternatively, commercial protamine also can cross-react and combine with human complement-fixing anti-protamine IgG antibody, producing so called "anaphylactoid" reactions (Weiss and Adkinson, 1991; Horrow, 1988; Lindblad, 1989; Horrow, 1985; Weiler et al., 1985). The complex formed between protamine and anti-protamine IgG antibody activates the complement system via the same cascade noted above in the non-immunological-mediated pathway. Previous studies suggested that antiprotamine IgG antibodies were predominantly of the complement-fixing IgG subclass (Gottschlich and Georgitis, 1988). Araphylactic reactions to protamine are far rarer than anaphylactoid responses.

Certain patient populations, such as diabetic patients receiving daily subcutaneous injections of protamine-insulin preparations, patients who receive protamine during cardiac catheterization and are then rechallenged following cardiopulmonary bypass, vasectomized patients, and patients who are allergic to fish, are at higher risk for developing adverse reactions to protamine. IgE antibodies to protamine have been identified in diabetics who exhibit anaphylacxis to the protamine component of NPH insulin (Dykewicz et al., 1994). Diabetics taking protamine containing insulin preparations have 4 to 8 times greater probability of a protamine reaction at the time of cardiac catheterization and 10 to 40 times greater probability of a protamine reaction at the time of surgery (Gupta et al., 1989; Gottchlich et al., 1988; Vincent et al., 1991). In a large multicenter meta-analysis (Levinson and Ohm, 1995), the incidence of protamine reaction at cardiac catheterization rose from 0.06% in non-diabetics to 0.6% (ten fold) in insulin-dependent diabetics, whereas in surgery the incidence rose from 0.12% in non-diabetics to 2.1% (twenty fold) in insulin-dependent diabetics. Nell and Thomas (1988) reported that 38% of NPH treated diabetics have IgG anti-protamine antibodies by ELISA assay. In a recently published article, Levinson and Ohm (1995) estimated that in insulin-dependent diabetes there was about 10 fold increased risk of a hemodynamically significant protamine reaction at the time of cardiac surgery, as compared to non-diabetic controls.

Since protamine is produced from the sperm of matured testes of salmon or related species of fish, theoretically individuals allergic to fish may have serum antibodies directed against protamine, or conversely, that commercial protamine preparations may be contaminated with other fish antigens that fish-allergic patients react to. To date, however, studies supporting the increased risk of protamine reactions in fish allergic patients are lacking and limited to case reports (Metz and Horrow, 1994; Weiss and Adkinson, 1991).

Male patients who are vasectomized are also at high risk for protamine reactions. Samuel et al., (1978b) showed that, with disruption of the blood-testes barrier following vasectomy, 22–30% developed autoantibodies against human proteins similar to protamine. Adourian and co-workers (Adourian et al., 1990) reported that 35% of vasectomized men have anti-protamine IgE antibodies in their serum compared to 0% in age matched controls. Sera from some vasectomized men that contain anti-protamine antibodies has been shown to cross-react with commercially prepared protamine as measured by a microcomplement fixation test (Samuel et al., 1978a). Recently, high titer protamine-specific IgG antibody has been identified in vasectomized patients associated with protamine induced anaphylaxis (Adourian et al., 1993).

Lakin et al. found that none of 22 hemaphoresis donors experienced reactions on their first exposure to protamine, whereas 4 of 11 donors experienced adverse responses on their second exposure to protamine following hemaphoresis (Weiss and Adkinson, 1991). Documentation that intravenous protamine exposure would create a risk for subsequent protamine exposure, however, is still lacking. The evaluation of the development of anti-protamine antibodies in a larger population of patients following the administration of a large dose of protamine is currently underway in certain clinical laboratories.

Inhibition of Carboxypeptidase N

As described previously, the primary reaction triggering the catastrophic protamine responses is the activation of the complement system, either through heparin-protamine complexes, or through protamine-antiprotamine IgG antibody interaction, with the subsequent liberation of anaphylatoxins. Once generated, anaphylatoxins can induce histamine release from human mast cells and basophils, cause neutrophil migration and smooth muscle contraction, initiate platelet aggregation, and stimulate thromboxane production from macrophages. A second factor that may contribute to the adverse reactions to heparin reversal with protamine is the nonapeptide bradykinin. Activation of Factor XII in blood (possibly by heparin) leads to the activation of plasma kallikrein with subsequent liberation of kinins from kininogen. Kinins also cause bronchoconstriction, hypotension, and increased capillary permeability.

Both kinins and anaphylatoxins have a C-terminal arginine (Erdos, 1962; Hugli, 1981). It is believed that most, although not all, of the activities of these peptides depend on this amino acid (Hugli, 1981; Tan et al., 1989). Carboxypeptidase N (CPN), which removes this C-terminal arginine residue, thus controls the activity of these peptides and convert them to the less active des arg metabolites. Recent data suggests that protamine can block the inactivation of kinins and anaphylatoxins by inhibiting the CPN, thereby potentiating these two factors implicated in the catastrophic reaction to protamine administration (Tan et al., 1989). The inhibition of CPN by protamine appears to come from two aspects (Tan et al., 1989): first, since protamine also possesses a C-terminal arginine residue, it functions as a competitive substrate inhibitor for CPN; and second, the sufficiently long chain length and polycationic nature of protamine allow it to bind CPN at sites close to the active center, resulting in partial blockage of the catalytic site.

Other Toxic Effects

Protamine has been shown to have anticoagulant properties when used in large doses (Kresowik et al., 1988), and is known to cause platelet aggregation and profound decrease in platelet counts (Jaques, 1973; Eika, 1972). Such effects may provide added toxicity to protamine, because they are capable of causing bleeding with standard or excessive use of protamine; especially if platelet numbers are already decreased, as may occur in surgical procedures where thrombocytopenia commonly accompanies major blood loss and replacement. The platelet aggregatory properties of protamine have been related to its polymeric and polycationic nature. The positively charged long chain of protamine has been shown to adhere to the negatively charged platelet membrane, thereby inducing platelet aggregation by forming "bridges" between adjacent platelets (Eika, 1972).

The anticoagulant properties of protamine have been more or less related to its effects on thrombin. In the elucidation of the mechanism of protamine-induced anticoagulation, Hansouna and co-workers (Cobel-Geard and Hassouna, 1983) show that protamine interacts with thrombin at its active site, and inhibits the inactivation of thrombin by antithrombin III. In addition, protamine exerts an inhibitory effect on thrombin in the conversion of fibrinogen to fibrin. Based on these findings, it is suggested that the mode of neutralization of thrombin by protamine is similar to the mechanism by which thrombin is inhibited by antithrombin III in its interaction with its natural substrate fibrinogen.

The present invention overcomes the type of limitations described above by providing protamine compositions that are bioactive, yet have reduced immunogenicity, antigenicity and/or toxicity compared to native protamine. The preferred bioactive, low-immunogenic, low-antigenic and low-toxic protamines are preferably low molecular weight protamines.

I. Preparation of LMWP

A. Selection of Protamine

Protamine consists of a group of heterogeneous polycationic peptides with an average molecular weight of about 4500 daltons. Protamine is found in sperm and in fertilized eggs from a variety of sources, including, but not limited to, mammals, amphibians and fish, with salmon and herring being the most common source. However, protamine has also been isolated from fertilized amphibian eggs (U.S. Pat. No. 5,187,260). Protamine from any of these sources is contemplated for use in the preparation of the instant LMWP compositions.

The amino acid compositions of two commercial protamine preparations are summarized in Table 1.

TABLE 1

Amino Acid Compositions of Protamine

| Amino Acid | No. of Residues in Protamine | |
|---|---|---|
| | Clupeine | Salmine |
| Arginine | 19 | 23 |
| Threonine | 2 | 0 |
| Serine | 3 | 3 |
| Proline | 6 | 3 |
| Alanine | 3 | 1 |
| Isoleucine | 1 | 1 |
| Valine | 2 | 2 |
| Glycine | 1 | 2 |
| Total | 37 | 35 |

Consistent with results reported elsewhere (Ando et al., 1973), these two heterogeneous protamine preparations show certain but not significant variations in their amino acid composition. Although clupeine protamine was used in preliminary studies due to its ready availability, salmine protamine can also be used for several reasons. One is that salmine protamine has a slightly higher arginine content, which provides suitable LMWP species with more potent heparin neutralization. The second reason, which is likely related to the first one, is that salmine protamine is the primary use in clinical practice. The third reason is that clupeine protamine contains more threonine and proline residues, which are among those amino acid residues that are most difficult to cleave with known proteases. Lastly, although both preparations are heterogeneous, salmine protamine is far more homogeneous than clupeine protamine (Ando et al., 1973), and thus produces more consistent LMWP products.

B. Selection of Protease

Trypsin and trypsin-like proteases, which catalyze hydrolysis of arginyl bonds, could lead to excess and/or uncontrollable protamine digestion, as well as production of too small peptides with unpredictable chain length. Thus, in most aspects of the present invention, these proteases are less preferred for use in digesting protamine.

The selection of thermolysin (EC 3.4.24.4) proves feasible in retaining the structural integrity of the arginine sequence and the minimal chain length of the peptide, both of which appear to be required for effective heparin neutralization. However, thermolysin cleaves certain specific amino acid residues (e.g. valine, isoleucine) at the N-terminal of the peptide bond. This could potentially result in the production of LMWP fragments with a potentially toxic C-terminal arginine group, should an arginine residue happen to reside at the N-end of the cleavage site. Thus, thermolysin is less preferred in instances where an N-terminal arginine residue is produced in the cleavage reaction. In addition, thermolysin does not hydrolyze alanyl or glycyl bonds, which occupy about 25% of the prospective, non-arginyl digestion sites in salmine protamine.

Thus, in certain aspects of the present invention, the plant protease ficin (EC 3.4.22.3) is preferred for use in the cleavage of protamine. Ficin is a 2.5 kDa enzyme that acts quite similarly as thermolysin, except that it is less specific than thermolysin (Liener and Friedenson, 1970). Ficin catalyzes the hydrolysis of glycyl, alanyl, valyl, and isoleucyl bonds (all of which are present in protamine; see Table 1 above), and of arginyl bond only under fairly vigorous conditions (which can be readily and completely avoided during the process of protamine digestion) (Kortt et al., 1974). In addition, ficin offers the advantage of digesting a protein at the C-end of the specific amino acid residues (Kortt et al., 1974), thereby avoiding the production of LMWP peptides with the potentially toxic C-terminal arginine group. The selection of ficin as a protease to prepare LMWP fulfills all three design criteria discussed above.

In instances where relatively large protamine fragments (e.g. >2000 daltons) are present following ficin digestion, which could be due to the presence of either serine or proline residues in these fragments, then other proteases, such as collagenase (EC 3.4.24.3), kallikrein (EC 3.4.21.34) and/or proline-specific endopeptidase, can be employed to further digest these large fragments. Collagenase cleaves the peptidyl bonds between two proline residues, kallikrein cleaves between an arginine and a serine residue, and proline-specific endopeptidase cleaves peptide bonds on the carboxy side of proline residues. These proteases, however, are known to be relatively specific, and only digest protamine if proline or serine is at the proper location. It should be pointed out that all the aforementioned proteases are presently available commercially from Sigma and/or ICN Pharmaceuticals, Inc.

II. Pharmaceutical Compositions and Kits

Pharmaceutical compositions of the present invention will generally comprise an effective amount of at least a first purified, bioactive protamine that has reduced immunogenicity or toxicity compared to native protamine, and is preferably of a low molecular weight, dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

A. Parenteral Formulations

The agents of the present invention will often be formulated for parenteral administration, e.g., formulated for injection via the intravenous, intramuscular, sub-cutaneous or other such routes. The preparation of an aqueous composition that contains one or more agents, such as low molecular weight bioactive protamine, will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Compositions comprising the agents of the present invention can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), dimethylsulfoxide (DMSO), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. Formulations are easily administered in a variety of dosage forms, such as the type of injectable solutions described above, but drug release capsules and the like can also be employed.

Suitable pharmaceutical compositions in accordance with the invention will generally include an amount of one or more of the agents of the present invention admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein. Moreover, for human administration, preparations should meet sterility, pyrogenicity, and general safety and purity standards as required by FDA Office of Biological Standards.

The therapeutically effective doses are readily determinable using an animal model, as shown in the studies detailed herein. Experimental animals susceptible to or having a bleeding condition or diabetes are frequently used to optimize appropriate therapeutic doses prior to translating to a clinical environment. Such models are known to be very reliable in predicting effective clinical strategies. The inventors have used such art-accepted animal models to determine working ranges of agents that provide beneficial therapeutic effects with minimal toxicity.

In addition to the compounds formulated for parenteral administration, such as intravenous or intramuscular injection, other pharmaceutically acceptable forms are also contemplated, e.g., tablets or other solids for oral administration, time release capsules, liposomal forms and the like. Other pharmaceutical formulations may also be used, dependent on the condition to be treated. Of course, methods for the determination of optimal dosages for conditions such as these would be evident to those of skill in the art in light of the dosage optimization methodology disclosed in the instant specification, and the knowledge of the skilled artisan.

As described in detail herein, it is contemplated that certain benefits will result from the manipulation of the agents of the present invention to provide them with a longer in vivo half-life. Slow release formulations are generally designed to give a constant drug level over an extended period. Increasing the half-life of a drug, such as agents of the present invention, is intended to result in high intravenous levels upon administration, which levels are maintained for a longer time, but which levels generally decay depending on the pharmacokinetics of the construct.

B. Therapeutic Kits

The present invention also provides therapeutic kits comprising the agents of the present invention described herein. Such kits will generally contain, in suitable container, a pharmaceutically acceptable formulation of at least a first low molecular weight bioactive protamine, in accordance with the invention. The kits may also contain other pharmaceutically acceptable formulations, such as any one or more of a range of therapeutically beneficial drugs. The kits will often further contain written instructions concerning the clinical and/or veterinary uses of the present invention.

The kits may have a single container that contains the agent, with or without any additional components, or they may have distinct container means for each desired agent. Certain preferred kits of the present invention include at least a first purified low molecular weight bioactive protamine that has reduced immunogenicity compared to native protamine, packaged in a kit for use in combination with the co-administration of a second agent, such as insulin. In such kits, the components may be pre-complexed, either in a molar equivalent combination, or with one component in excess of the other; or each of the components of the kit may be maintained separately within distinct containers prior to administration to a patient.

When the components of the kit are provided in one or more liquid solutions, the liquid solution is an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container means. One of the components of the kit may be provided in capsules for oral administration.

The container means of the kit will generally include at least one vial, test tube, flask, bottle, syringe or other container means, into which the protamine, and any other desired agent, may be placed and, preferably, suitably aliquoted. Where additional components are included, the kit will also generally contain a second vial or other container into which these are placed, enabling the administration of separated designed doses. The kits may also comprise a second/third container means for containing a sterile, pharmaceutically acceptable buffer or other diluent.

The kits may also contain a means by which to administer at least a first purified low molecular weight bioactive protamine that has reduced immunogenicity compared to native protamine to an animal or patient, e.g., one or more needles or syringes, or even an eye dropper, pipette, or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

C. Combination of LMWP With Therapeutic Proteins

As described herein, protamine has been used to prolong the adsorption of a variety of therapeutic proteins, most notably insulin and α-interferon (U.S. Pat. No. 4,853,218). Without being held to any particular mechanism of action, protamine, which has a $pK_a$ of about 10, is believed to form insoluble complexes with proteins that have an acidic $pK_a$ (the $pK_a$ of insulin is about 4.5) by neutralizing the $pK_a$ to about 7 or about 7.5 or so.

Therefore, the LMWP compositions described herein are contemplated for use in forming sustained release compositions with therapeutic proteins having an acidic $pK_a$, including, but not limited to, insulin and α-interferon.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Low Molecular Weight Protamine

In this example, low molecular weight protamine (LMWP) fragments were derived from native protamine by enzymatic digestion of protamine with thermolysin. Then, the heparin-neutralizing ability of the LMWP fragments was examined in vitro, using a electrochemical sensor method and various biological assays. Next, the immunogenicity and antigenicity of the LMWP species were examined in mice, using an appropriately selected enzyme-linked immunosorbent assay (ELISA). The enzymatic digestion of protamine yields LMWP that contained anti-heparin activity but lacked antigenicity and immunogenicity.

A. Materials and Methods

Protamine sulfate (Clupeine from herring), 2,4,6-trinitrobenzene sulfonic acid (TNBS), thermolysin (EC 3.4.24.4), Freund's adjuvant, and goat-antimouse-IgG-alkaline phosphatase were purchased from Sigma Chemical Co. (St. Louis, Mo.). Porcine intestine heparin (169 IU/mg; average molecular weight of 13,000 daltons), antithrombin III (ATIII), factor Xa, and chromogenic substrate S-2238 were obtained from Pharmacia Hepar Inc. (Franklin, Ohio). Actin cephaloplastin was obtained from Dade (Miami, Fla.). The Coomassie Plus reagent for Bradford protein assay was purchased from Bio-Rad Laboratories (Richmond, Calif.). Freshly frozen human plasma in citrate was obtained from American Red Cross in Detroit, Mich.

Preparation of Low Molecular Weight Protamine (LMWP) Fragments

For monitoring purpose, protamine at first was labeled with 2,4,6-trinitrobenzene sulfonic acid (TNBS) to yield absorbance at 340 nm (Ando et al., 1973). One-half gram of protamine was dissolved in 1 ml of 0.17 M borate buffer at pH 8.1, and then mixed with 3 ml of TNBS solution (0.2 g/ml). After incubation in the dark for 3 h at 25° C., the reaction was quenched by the addition of 100 μl of 0.1 N HCl. The TNBS-labeled protamine was purified by an automated FPLC System (Model LCC-501 Plus System, Pharmacia Biotech Inc., Piscataway, N.J.) equipped with a Sephadex G-25 column (16×500 num). The elution buffer was 50 mM Tris-HCl, pH 8.1 containing 0.01 M CaCl.

Following purification, the TNBS-labeled protamine was digested with thermolysin by using a protamine concentration at least 100 times higher than that of thermolysin. The reaction mixture was incubated in the dark for 3.5 h at 40° C., followed by rapid heating in a boiling bath. An aliquot of the digested protamine was fractionated on a Sephadex G-25 column by using the same FPLC system as mentioned above. The elution profile of the LMWP fragments was monitored by measuring the absorbance of TNBS at 340 nm. After the elution profile has been established, the LMWP fragments for subsequent studies were prepared in the same fashion as described above except for protamine that was not labeled with TNBS. The concentration of protamine and LMWP was determined by the method (Bradford, 1976), using the Coomassie Plus dye reagent (Bio-Rad Labs, Richmond, Calif.).

Heparin Neutralization Measured by the Heparin Sensor Method

The heparin sensor was prepared as follows (Ma et al., 1993). In brief, a specially formulated poly(vinyl chloride) (PVC) membrane doped with tridodecylmethyl-ammonium chloride (TDMAC) was cast and then incorporated onto a Phillips electrode body (IS-561, Glasblaserei Moller, Zurich, Switzerland). A 0.015 M NaCl solution was used as the internal reference electrolyte solution. The potentiometric response of the membrane electrode was measured relative to an external double junction Ag/AgCl reference electrode, using a Fisher Scientific Accumet pH meter (Model 910). The sample solution was stirred constantly and potential change ($\Delta E$) was measured 5 min after the addition of heparin.

To measure heparin neutralization by LMWP, the heparin sensor was placed in 50 ml of a buffer solution containing 50 mM Tris-HCl, 0.12 M NaCl at pH 7.4. While stirring, 100 $\mu$l of LMWP solution (2 mg/ml) was added, followed by the addition of 100 $\mu$l of heparin solution (1 mg/ml). The buffer solution to which only heparin was added served as the control, and 100% of heparin neutralization was defined as the reversal of electrochemical potential of this heparin solution back to where after sufficient amount of normal protamine was added.

Heparin Neutralization Measured by Chemical/Biological Assays

Heparin neutralization by protamine and LMWP was also measured in plasma by anti-factor Xa chromogenic assay and activated partial thromboplastin time (aPTT) clotting assay (Yang et al., 1986). In brief, for the anti-factor Xa assay, a series of plasma samples containing 0.4 mg of heparin, 15 IU of ATIII, and various amounts of protamine (0–0.8 mg) or LMWP (0–0.4 mg) were prepared. One hundred microliters of the plasma sample were then mixed with 800 $\mu$l of Tris-HCl buffer (pH 7.4), followed by the addition of 100 $\mu$l of Factor Xa (7.1 nkat/ml). After a 3 min incubation at 37° C., 200 $\mu$l of S-2238 substrate (0.5 mg/ml) were added. The reaction mixture was incubated for 5 min at 37° C. and then quenched by the addition of 200 $\mu$l of 20% acetic acid. The absorbance in the solution was measured at 405 nm, and the degree of heparin neutralization is proportional to this measured absorbance.

For the aPTT clotting assay, 15 $\mu$l of heparin solution (20 $\mu$g/ml) was mixed with 15 $\mu$l of solution containing various concentrations of protamine (0–60 $\mu$g/ml) or LMWP species (0–100 $\mu$g/ml). To the mixture, 100 $\mu$l of actin cephaloplastin and 100 $\mu$l of plasma were added. After 3 min of incubation, 100 $\mu$l of 0.02 M calcium chloride (preheated to 37° C.) was added and the clotting time was immediately measured using a fibrometer (Fibrosystem, Becton Dickinson Company, Cockeysville, Md.).

Immunogenicity/Antigenicity Studies

The immunogenicity of protamine and LMWP was examined in mice. The production of polyclonal antibodies was performed as described (Cooper and Paterson, 1991). Fifteen thin-skinned albino mice, ten for protamine and five for LMWP were included. Each mouse was immunized with 50 $\mu$g of either protamine or LMWP in the complete Freund's adjuvant (CFA). Four weeks later, animals were bled and first booster was given with 5 $\mu$g of protamine (or LMWP) in incomplete Freund's adjuvant (IFA). Second and third boosters were given at two-week intervals. Afterwards, blood was collected, allowed to clot, and centrifuged to collect serum. All sera were tested for IgG antibodies using a modified ELISA method (Singh et al., 1982). Protamine or LMWP was used to coat the wells of the microplate in order to capture their related antibodies. The detection antibody was goat-antimouse-IgG-alkaline phosphatase that was reacted with p-nitrophenylphosphate to produce the absorbance readings at 405 nm. The antigenicity of LMWP was examined by following the same ELISA method described above but by utilizing a LMWP-coated microplate for antibody detection in the protamine-immunized mice.

B. Results

Figure 2:
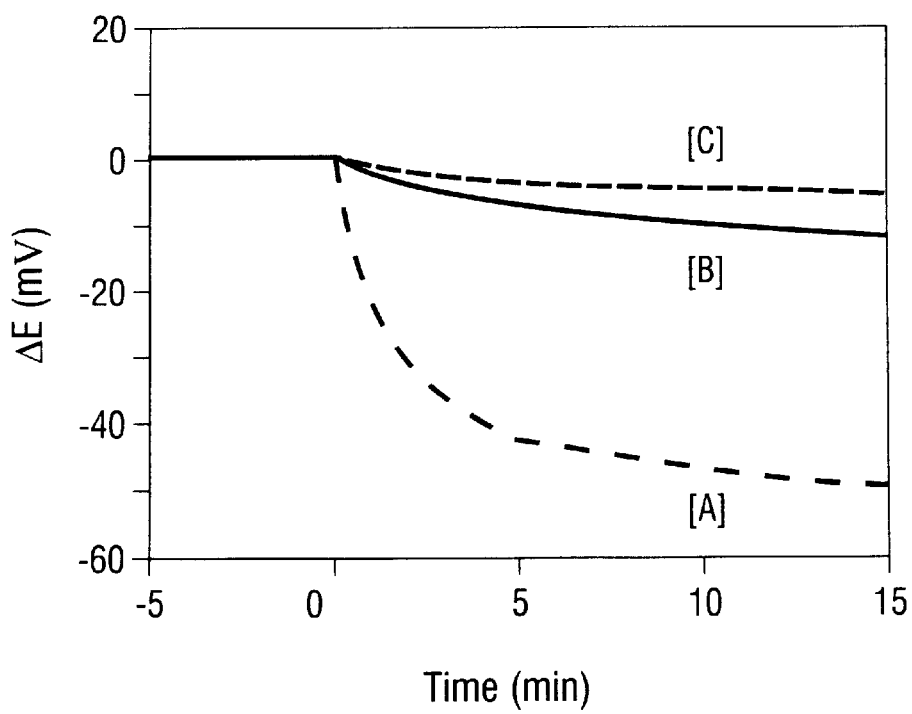
FIG. 2. Potentiometric response (DE, mV, vertical axis) measured by a heparin sensor of a solution containing 25 IU heparin (A), 25 IU heparin+0.4 mg thermolysin-digested protamine (B) and 25 IU heparin+0.4 mg of normal protamine (C), as a function of time (min, horizontal axis).

Protamine does not adsorb light in the ultraviolet region because it does not contain aromatic amino acid residues. Thus, in order to monitor FPLC elution profiles, protamine was first labeled with TNBS to yield absorbance at 340 nm. The TNBS-labeled protamine was digested with thermolysin, a protease that does not cleave the arginyl bonds. The primary reason of selecting thermolysin was to avoid excess digestion and retain the structural integrity of the arginine sequence in protamine. In addition, protamine was already known to contain a few cleavable sites (e.g., Val, Leu, etc.) for this enzyme (Ando et al., 1973). FIG. 1 depicts the elution profiles from a Sephadex G-25 column of native protamine (first peak) and thermolysin-treated protamine (second peak). The shift of the protamine peak towards the right indicated that the thermolysin-treated protamine was a low molecular weight preparation. This was referred to as the low molecular weight protamine (LMWP), which showed a molecular weight distribution in the range of 400 to 1,400 daltons with the peak around 1,200 daltons To verify that it only requires a specific fragment of protamine and not the entire protamine to yield a full neutralization of heparin, a previously developed electrochemical heparin sensor was utilized as the analytical tool. The sensor yielded a significant negative potentiometric response ($\Delta E = -40$ mV) to heparin at clinically relevant concentrations (0.5–10 unit/ml) (Ma et al., 1993). This potentiometric response, however, was reversed towards the baseline when heparin was neutralized with protamine (Ma et al., 1993). Results in FIG. 2 show that when the thermolysin-treated protamine was added to a solution containing heparin, the initial potentiometric response to heparin was also reversed to nearly the same level as that when protamine was used as the neutralizing agent. Previous clinical studies (Wahr et al., 1996) had demonstrated that measurements of the degree of heparin neutralization using this potential change ($\Delta E$) method correlated well with that using the blood clotting time (Wahr et al., 1996). Thus, the finding in FIG. 2 implicitly confirms that the thermolysin-digested, chain-shortened protamine still retains its full ability in neutralizing heparin.

Figure 3:
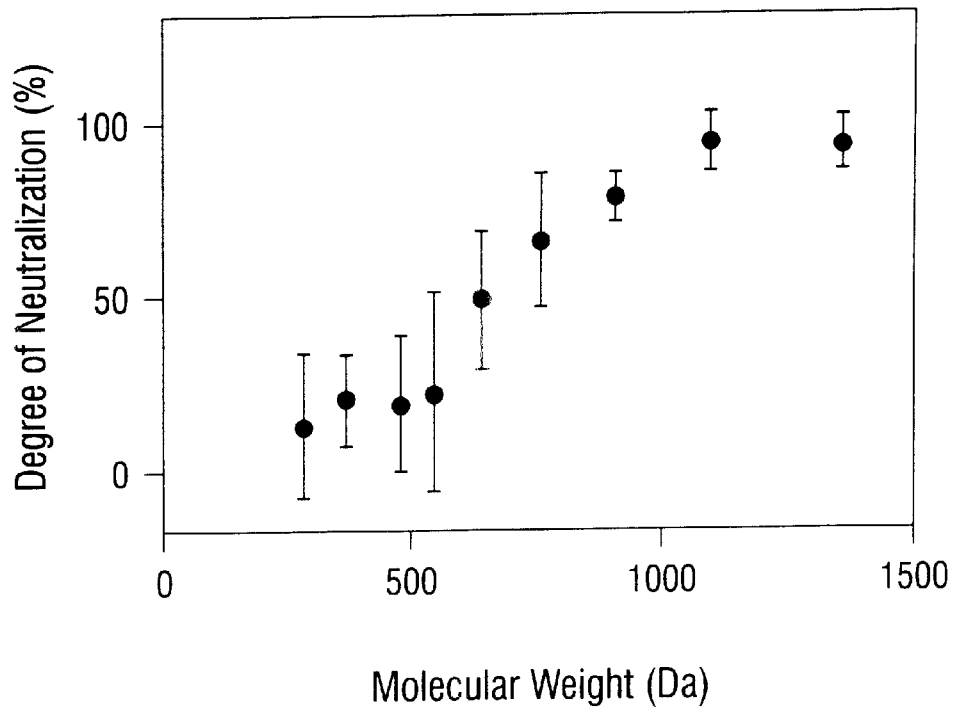
FIG. 3. Relationship between the relative binding affinity to heparin and the molecular weight of thermolysin-digested protamine. Relative binding to heparin was determined by measuring the potential change in a heparin solution (25 IU) after the addition of digested protamine. A 100% of binding affinity was assumed for untreated protamine. Degree of heparin neutralization (%) is shown on the vertical axis, and the molecular weight (Da) of the thermolysin-digested protamine is shown on the horizontal axis.

The individual fractions of the thermolysin-digested protamine seen in FIG. 1 were collected and tested for ability to neutralize heparin using the same sensor method. FIG. 3 illustrates the relationship between the degree of heparin neutralization (assuming a 100% neutralization for untreated protamine) and the molecular weight of LMWP fragments. The degree of heparin neutralization increased with the increasing molecular weight of LMWP and reached a plateau (100% neutralization) after a molecular weight of approximately 1,100 daltons (FIG. 3). These results suggest that the LMWP fragments with a molecular weight as low as 1.1 kDa still retain their full ability of heparin neutralization.

The fraction numbers #15 through #18 in FIG. 1, which yielded 100% heparin neutralization and possessed a molecular weight of 1.1–1.3 kDa, were pooled for subsequent studies. This "pooled fraction" was not homogeneous and contained at least 3 to 4 LMWP fragments as resolved by reverse-phase chromatography. This finding was somewhat anticipated considering the heterogeneous nature of protamine even prior to its proteolytic digestion. The amino acid analysis of this pooled fraction revealed a composition of 5–6 arginine, 1 proline, 1 serine, and 1 alanine residues, along with trace amounts of threonine, valine, and glycine residues. These results are in good agreement with those reported by other investigators for thermolysin-treated protamine fragments with similar molecular weights (Ando et al., 1973).

These studies suggest that six arginine residues will be the minimum requirement of LMWP for complete neutralization of heparin activity. This conclusion is consistent with literature findings on the binding of heparin with ATIII (Smith and Kanuer, 1987; Cardin and Weintraub, 1989). Both the experimental results (Smith and Kanuer, 1987) and theoretical prediction (Cardin and Weintraub, 1989) suggest that a sequence containing at least 4 to 5 basic amino acid residues is required for ATIII to bind effectively with heparin. It is therefore reasonable to assume that more than five arginine residues are required for LMWP to neutralize heparin, especially since neutralization necessitates a stronger binding to heparin than that of ATIII in order to displace ATIII from heparin.

Figure 4:
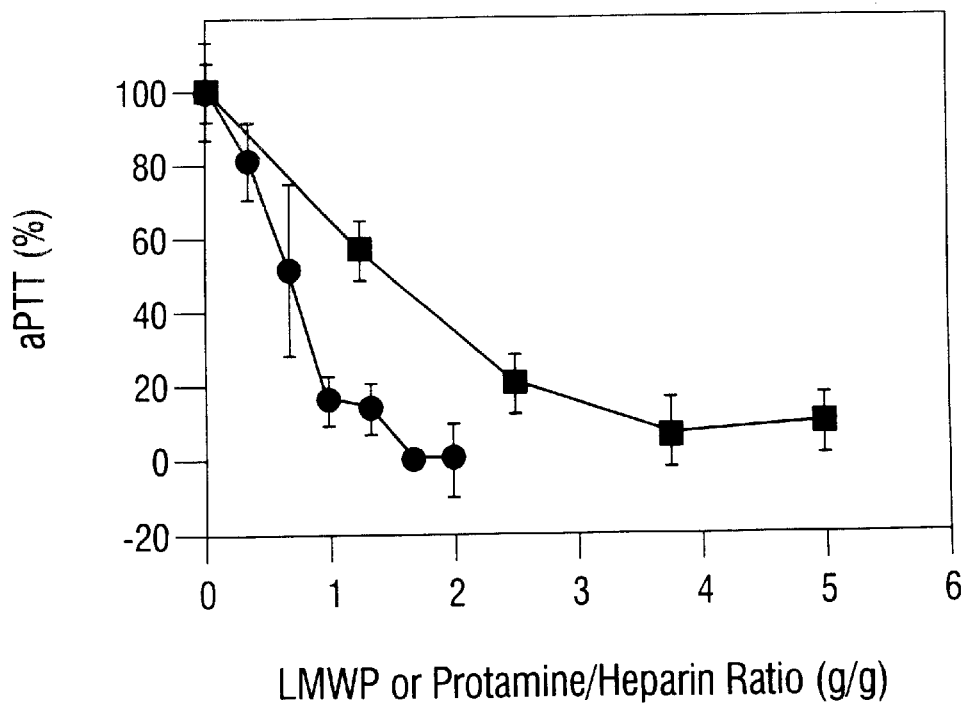
FIG. 4. Neutralization of heparin by protamine (■) and LMWP (●), as measured by the aPTT clotting assay. The aPTT (%) is shown on the vertical axis, and the ratio (g/g) of protamine or LMWP to heparin is shown on the horizontal axis.

Although the sensor method can measure the extent of heparin neutralization as accurately as the clotting time-based heparin assays (Wahr et al., 1996), it is still a method that measures chemical binding but not the biological function of heparin during neutralization. To further evaluate these biological functions, neutralization of heparin by LMWP was studied using the conventional aPTT clotting assay and anti-Xa chromogenic assay. As shown in FIG. 4, both protamine and LMWP effectively neutralized heparin-induced aPTT activity. The LMWP, however, was not as effective as protamine since twice as much of LMWP (~3.7 mg) as the protamine (~1.7 mg) was required to completely neutralize the aPTT activity of heparin (1 mg). This finding is somewhat anticipated considering the non-specific nature of the aPTT assay. The aPTT assay is a general method based on the measurement of activation of the intrinsic system of the coagulation cascade (Walenga et al., 1986). A wide variety of coagulation factors including thrombin are involved in the neutralization of the aPTT activity. It is therefore of no surprise that LMWP with its significantly shortened chain length would require a much higher dose to completely displace thrombin from its binding to heparin as reflected by the aPTT study.

Figure 5:
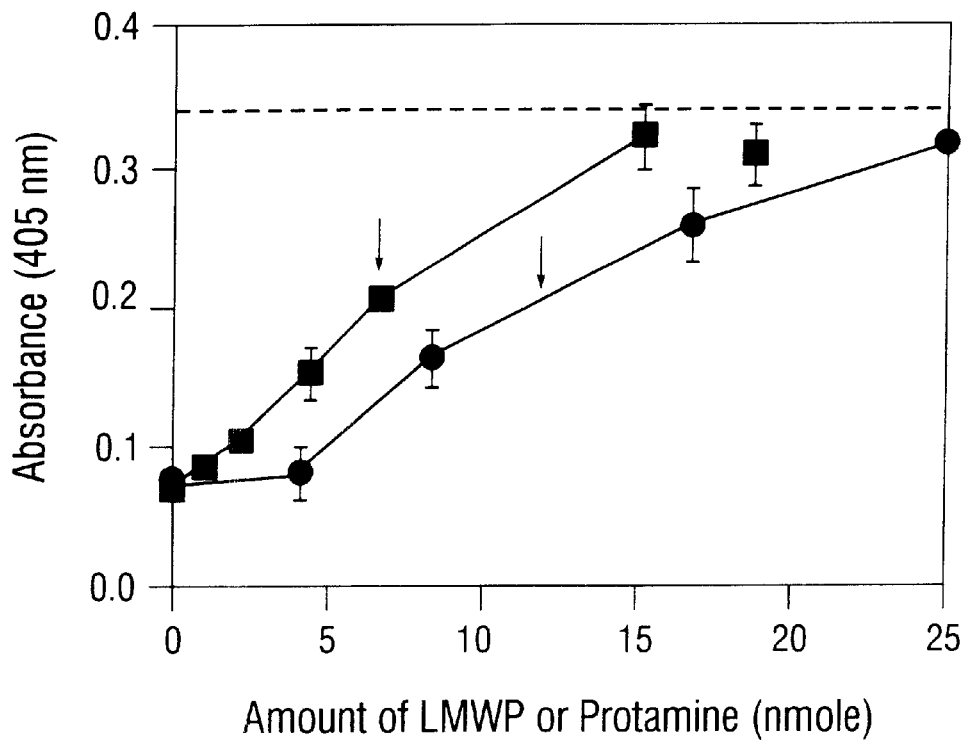
FIG. 5. Neutralization of heparin by protamine (●) and LMWP (■), as measured by the anti-Xa chromogenic assay. The absorbance at 405 nm is shown on the vertical axis, and the amount of protamine or LMWP (nmole) is shown on the horizontal axis. The dashed line represents control (100% neutralization), and the arrows indicate 50% neutralization.

Interestingly, FIG. 5 shows that LMWP was more effective than protamine (on a weight basis) in neutralizing anti-Xa activity of heparin, as measured by the chromogenic assay using S-2222 as the specific substrate. A complete neutralization of the anti-Xa activity of the same dose of heparin (40 $\mu$g) was achieved with 63 $\mu$g (14 nmole) of protamine; however, only 30 $\mu$g of LMWP were required. These estimated neutralization end-points appear to be reliable and consistent, since the doses required for 50% heparin neutralization (shown by arrows and determined as the half-points of $\Delta$Abs(450 nm) in FIG. 5) occurred precisely at one-half of the doses (i.e. 7 nmole and 13 nmole for protamine and LMWP, respectively) required for 100% neutralization.

Immunogenicity of both protamine and LMWP was examined in mice by monitoring the production of polyclonal antibodies. Although the antibody titer was not very high (only 1:50 dilution), 4 out of 10 mice showed a positive reaction for antibodies to protamine (see the hatched bars in FIG. 7). On the other hand, none of the five mice immunized with LMWP exhibited any detectable evidence for antibody production, when examined using the LMWP-coated wells.

The antigenicity of LMWP, which is defined as its ability to be recognized by anti-protamine antibodies, was also examined by utilizing the same ELISA method but by using a LMWP-coated microplate for antibody detection in protamine-immunized mice. As shown by the open bars in FIG. 7, anti-protamine antibodies exhibited extremely low level of cross-reactivity, if any at all, towards LMWP, with the absorbance readings less than one-tenth for LMWP when compared to those for protamine. These studies confirm that LMWP derived from protamine with a molecular weight of approximately 1,200 daltons is markedly devoid of its immunological properties.

EXAMPLE 2

Heparin Neutralization and Complement Activation by LMWP

A. Neutralization of Heparin/LMWH

Neutralization of the anticoagulant functions of both heparin and LMWH by protamine and LMWP is studied in human plasma using the aPTT clotting assay and the chromagenic anti-Xa and anti-IIa assays (Yang et al., 1986). The aPTT values of the test samples, are measured using a fibrometer (Fibrosystem; Becton-Dickinson, Cockeysville, Md.), and the anti-Xa and anti-IIa activities are measured using the chromagenic substrates S-2222 and S-2238, respectively. Unless otherwise stated, heparin powder (MW~15,000 Da; Anticoagulant activity: 167 IU/mg; Anti-Xa activity: 110 IU/mg; Anti-IIa activity: 85 IU/mg) from Pharmacia-Hepar (Franklin, Ohio) and Enoxaparin powder (MW~4400 Da; Anticoagulant activity: 32 IU/mg; Anti-Xa activity: 96 IU/mg; Anti-IIa activity: 27 IU/mg) by Rhone-Poulenc Rorer (Collegeville, Pa.) are used for these studies. The neutralizing activity of LMWP towards heparin or LMWH on a specific coagulation parameter (e.g. anti-Xa activity) is compared on a weight basis with that of protamine.

B. Complement Activation

Heparin-protamine complexes (HPC), similar to antigen-antibody complexes, activate complement system by the classical pathway but not by the alternate pathway (Rent et al, 1975; Cavarocchi et al., 1985). This activity has been regarded as one of the primary nonimmune reactions of protamine when used as an anti-heparin agent (see above). Activation of the complement cascade results into total depletion of hemolytic activity ($CH_{50}$), leading to the liberation of anaphylatoxin C3a, C4a and C5a. The prelude to such an event is the binding of HPC to C1q (Rent et al., 1975), which requires a critical size for HPC to initiate (Cavarocchi et al., 1985). LMWP, with its markedly reduced chain length, has reduced crosslinking with heparin (and particularly with LMWH, which is also shortened in its chain length) and thus forms fewer aggregates with sufficient size to bind with C1q. Thus, LMWP induces significantly less complement activation. This is studied by determining the total hemolytic complement consumption ($CH_{50}$) and the binding of C1q by the heparin (LMWH) and LMWP (protamine) complexes.

Total Hemolytic Complement Assay

The total hemolytic complement assay is based on the measurement of complement-mediated hemolysis of sheep red blood cells (SRBC) presensitized with SRBC antibody (hemolysin). The level of hemolysis is expressed in terms of the level of serum dilution that causes 50% of cells to lyse, known as $CH_{50}$. For these studies, heparin, LMWH, protamine, and LMWP alone, as well as complexes of heparin-protamine, LMWH-protamine, heparin-LMWP, and LMWH-LMWP, instead of serum, are used to determine the $LD_{50}$ required for $CH_{50}$ (Yang et al., 1991b; Yang et al., 1991a). Comparison is made among these eight compounds, particularly between protamine and LMWP and their conjugates with two different types of heparin. Since complement components are extremely unstable proteins, special attention is paid to handling and storage of blood and all other reagents. Blood is allowed to clot, centrifuged, and assayed fresh or stored immediately at −70° C.

C1-Binding Assay

Quantitation of the C1 binding of the above 8 compounds is conducted using the microplate-ELISA method (Singh and Tingle, 1982). For the four conjugates, protamine (or LMWP) will be combined with heparin (or LMWH) at four different ratios including 1:1, 2:1, 4:1, and 8:1, and all of these combinations are tested for C-1 binding. Human C1 and antibodies to C1 are available from Calbiochem (La Jolla, Calif.).

C. Assays

General Assays

An electrochemical sensor that yields specific and significant response to protamine in buffer and undiluted plasma has been demonstrated to respond not only to protamine but also to synthetic peptides containing as little as four to five arginine residues (U.S. Pat. No. 5,607,567). The protamine sensor yields a similar response to thermolysin-generated LMWP on the same weight basis. Thus the protamine sensor can be employed as a general tool to monitor LMWP species, as long as these species carry at least 4 arginine residues.

Specific Assays for Desired LMWP

As discussed above, those LMWP fragments that possess a heparin-binding strength greater than that between heparin and ATIII are capable of neutralizing the anticoagulant function of heparin. To facilitate the identification of such fragments, the inventors have designed a rapid and yet specific and precise assay utilizing the above protamine sensor as the detection probe. Like the results observed with the heparin sensor, the potentiometric response to protamine is also reversed towards the baseline when protamine is neutralized by heparin.

Thus, the new assay measures the potential change (with the protamine sensor) of a solution containing a known quantity of an LMWP test sample before and after the addition of a negligible volume of a concentrated heparin-ATIII mixture (ATIII in excess). If the LMWP species carries the required heparin-binding strength, then it displaces ATIII and is neutralized by heparin, eliciting a reduction in the potentiometric response. Otherwise, the EMF response to LMWP remains unchanged. By measuring the potential change of the test sample, the desired LMWP fragments are rapidly and precisely identified. In addition, the change in electrochemical potential is also used to quantitate the heparin-neutralizing activity of the LMWP species. Previous studies have shown that the heparin-neutralizing activity of protamine determined by the sensor method correlates well with that determined by the conventional blood clotting assay (Wahr et al., 1996). To confirm these results, the desired LMWP species, once screened and identified by the new assay, is subjected to the conventional aPTT clotting assay and the chromogenic assays to validate their heparin-neutralizing ability.

D. Results

1. Neutralization of Heparin and LMWH by Protamine and LMWP

Figure 6:
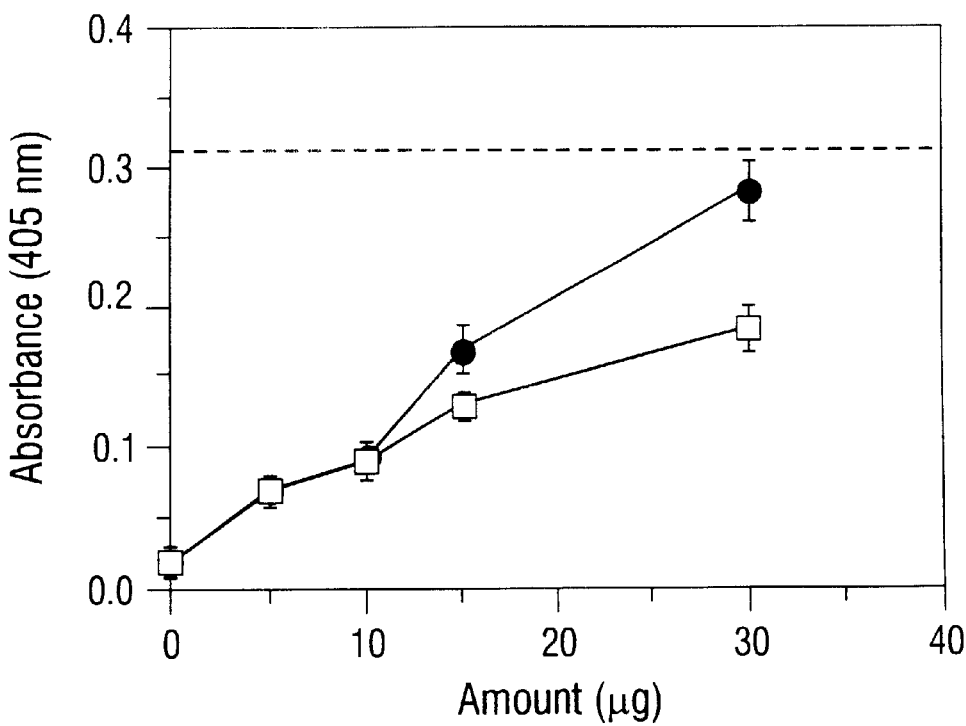
FIG. 6. Neutralization of LMWH (CY 216) by protamine (□) and LMWP (●), as measured by the anti-Xa chromogenic substrate assay. The absorbance at 405 nm is shown on the vertical axis, and the amount of protamine or LMWP (μg) is shown on the horizontal axis. The dashed line represents control (100% neutralization).

Studies involving the neutralization of the anti-Xa activity of LMWH by both protamine and LMWP were conducted. As seen in FIG. 6, LMWP was more effective than protamine in neutralizing the anti-Xa activity of CY216 (a LMWH fragment from Sanofi Recherche, Gentilly Cedex, France, with an average MW of 2500 daltons). At a same dose of 30 µg, LMWP completely neutralized the anti-Xa activity of CY216 whereas protamine only yielded 60% neutralization.

With the assistance of the heparin sensor and the methodology described previously (Yun et al., 1993), the inventors were able to determine the binding constant of heparin and LMWH to ATIII, protamine, and LMWP. As shown in Table 2, LMWH possesses the same specific ATIII-binding domain as that of native heparin, thereby yielding a similar binding strength to ATIII ($5 \, \mu M^{-1}$) as that of heparin.

TABLE 2

Binding Constants of Heparin and
LMWH to ATIII, Protamine and LMWP

| | Binding Constant ($\mu M^{-1}$) | |
|---|---|---|
| Species | Heparin | LMWH |
| ATIII | 5.6 + 1.2 | 5.0 + 1.7 |
| Protamine | 89.0 + 2.0 | 1.1 + 0.3 |
| LMWP | 40.0 + 6.0 | 24.0 + 2.1 |

On the other hand, the chain-shortened LMWH carries much less negative charges than native heparin, thereby yielding a much weaker binding strength (i.e. $1.1 \, \mu M^{-1}$) to protamine than native heparin (i.e. $89 \, \mu M^{-1}$). In fact, the binding constant between LMWH and protamine is actually lower than that between LMWH and ATIII. This explains why protamine does not have sufficient strength to fully displace ATIII from LMWH and neutralize the anti-Xa activity of LMWH, as clearly documented in the literature (Harenberg et al., 1985; Diness and Ostergaard, 1986; Wakefield et al., 1994). The LMWP species, however, possesses the required charge density and structural conformation to bind tightly to the specific pentasaccharide sequence, as reflected by its stronger binding constant ($24 \, \mu M^{-1}$) to LMWH than that of the native protamine ($1.1 \, \mu M^{-1}$). Since this binding constant exceeds that between heparin (and also LMWH) and ATIII, LMWP is more effective in neutralizing the anti-Xa activity of both heparin and LMWH.

2. Complement Activation

Complement activation by the heparin/protamine and heparin/LMWP complexes were measured by the $CH_{50}$ assay (Singh and Tingle, 1982). A 20% plasma solution was used for all the studies, because this percentage of plasma was found to provide the maximal magnification of the change in $CH_{50}$ values. Ten USP units of heparin were combined with 100 µg of protamine, whereas the same amount of heparin was combined with 350 µg of LMWP. In both preparations, the aPTT and ant-Xa activity of heparin were completely neutralized. Preliminary results showed that while the heparin/protamine preparations resulted in a reduction of the $CH_{50}$ values by 86±5%, the heparin/LMWP preparations only produced a depletion of the $CH_{50}$ values by 12±2%. These results suggest that LMWP induces less activation of the complement system than whole protamine.

EXAMPLE 3

Combination of LMWP With Insulin

Among the four groups of patients at high risk to protamine responses, the diabetic patients represent the largest population. Since the underlying cause for the risk is related to the immunogenicity of the administered commercial protamine, the use of LMWP, if proven to be less immunogenic, for insulin formulation would be of significant benefit to this group of patients. To examine this possibility, LMWP was conjugated with insulin and then tested in diabetic rats for the control of blood glucose levels.

Protamine prolonged insulin's adsorption by the formation of a complex (PZI or NPH) that is not soluble at physiological pH (the complex has a pI of 7.4). To examine whether LMWP provides the same function, insulin (80 USP U/ml) and LMWP (1 mg/mL) solutions were combined at pH 7.4 in different volume ratios, followed by measuring the turbidity of these solutions at 350 nm. The volume ratio of 1:8 of insulin:protamine yielded the highest turbidity and was therefore selected for subsequent animal studies.

Figure 8:
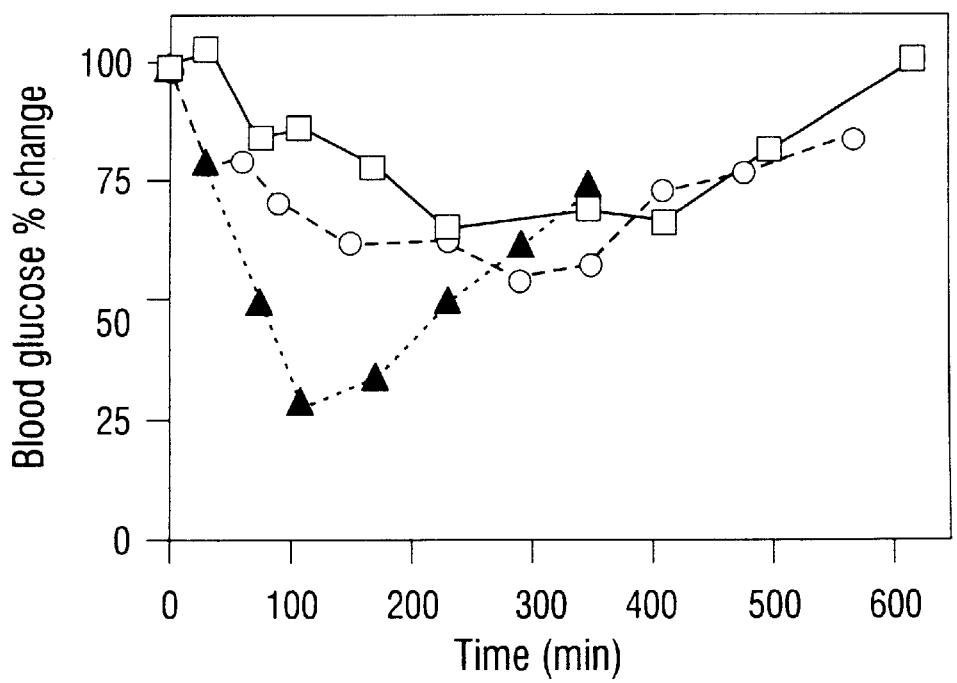
FIG. 8. The time-dependent change of blood glucose levels in diabetic mice receiving insulin only (▼), protamine-insulin (□) and LMWP-insulin (○).

Induction of diabetes in rats was carried out by the injection of streptozotocin at a dose of 45 mg/kg body weight. Diabetes was confirmed 24 h after injection by measuring the tail blood glucose with a Lifescan Glucometer (One Touch II). FIG. 8 presents a representative figure of the time-dependent change in blood glucose levels in a diabetic rats that was given insulin, protamine-insulin, and LMWP-insulin. As shown, insulin preparations containing either protamine or LMWP has significantly extended the time require to reach the minimum glucose level, as well as the overall time span to preserve a low glucose level than the preparations containing insulin alone. Analysis of the data obtained from 6 rats show that the time required to reach the minimum glucose level for insulin alone, protamine-insulin, and LMWP-insulin were 100±20, 220±70 and 270±20 min, respectively; whereas the overall time span to preserve a low glucose level for the same three preparations were 360±50, 570±20, and 620±40 min, respectively. These results clearly demonstrate that LMWP retains the same, if not superior, ability of protamine in retarding insulin adsorption.

EXAMPLE 4

Further Studies With LMW

The ideal heparin-neutralizing agent most clinicians would prefer and yearn for would be an intravenous drug providing all the advantages of protamine, yet lacking anaphylactic potential and preserving hemodynamic stability when infused (Metz and Horrow, 1994). The present Example details: [1] the efficacy and toxicity of LMWP in vitro using biochemical and biological assays, and the antigenicity of LMWP using human anti-protamine antibodies obtained from diabetic patients; [2] the efficacy and toxicity of LMWP in vivo using dog as the animal model; and [3] the immunogenicity and the pharmacokinetics/biodistribution of LMWP in vivo using mouse and rat as animal models, respectively. These studies are performed using both heparin and LMWH as the anticoagulant compounds.

LMWP fragments offer advantages to supersede protamine as the new generation of potent and yet non-toxic heparin antagonists. The instant LMWP retains at least the same charge "density" (i.e. availability) as that of protamine, thereby inheriting an equivalent potency in heparin neutralization. These peptide fragments, however, have significantly less net charge, producing less non-immunological-mediated adverse side effects.

From a pharmacological perspective, LMWP also enjoys advantages over its parent drug, protamine. The use of LMWP as the heparin-neutralizing agent actually converts the protamine therapy from a large protein to a small peptide drug. The modification of a macromolecular protein drug to a small peptide results in altered pharmacokinetics and bioavailability in favor of the therapeutic as opposed to the toxic effects of the drug.

The prelude to almost all of heparin-induced anticoagulant events is its binding with ATIII. A key to heparin neutralization is, therefore, to detach this interaction. In other words, in order for LMWP to effectively neutralize heparin, it should possess a binding strength to heparin that exceeds that between heparin and ATIII. Thus one design criterion for LMWP is to achieve this required heparin-binding strength. This is shown above in Example 2.

A second criterion is that in order to minimize the possibility for immunogenicity, antigenicity, and other toxic effects resulting from the bridging property of protamine, the LMWP molecule should be designed as small as possible. The presence of a C-terminal arginine residue in certain peptides has been related to their vasoactivity. Thus a third criterion is to create a LMWP fragment without this C-terminal arginine group.

A. LMWP Preparations for In Vitro and In Vivo Studies

To prepare LMWP for in vitro and in vivo studies, the protamine is first digested with a protease, as described above, followed by the purification of desired LMWP by using a gel filtration and a heparin-affinity chromatography.

Protease Digestion

An investigation of the optimal digestion time and molecular weight distribution of the completely digested protamine is conducted. To facilitate the monitoring process, protamine is labeled with trinitrobenzene sulfonic acid (TNBS). TNBS has been used widely to label the terminal —$NH_2$ group in protein sequencing (Suzuki and Ando, 1968). The trinitrophenyl derivatives thus formed can be detected directly at 340 nm. An appropriate amount of protease (such as ficin) is added to a protamine solution, and at various times a sample is withdrawn and passed through a fully automated Pharmacia FPLC system (Model S) equipped with a 16×500 mm Sephadex G-25 column (fractionation range 1,000–5,000 daltons). The optimal digestion time is reached when a stable elution profile is observed. The molecular weight of each fraction is determined using the low molecular weight internal protein markers obtained from Pharmacia-Upjohn (Kalamazoo, Mich.). It should be pointed out that ficin, with a molecular weight of 25,000 daltons, elutes in the void volume of the Sephadex G-25 column and thus does not contaminate any of the digested protamine fractions.

If the amino acid sequence published previously for salmine protamine (Ando et al., 1973) is correct, then a completely ficin-digested protamine yields 5 to 6 LMWP fragments with a molecular weight ranging from 680 to about 1,400 daltons. If fraction(s) with a relatively large molecular weight (e.g. >2000 daltons) are observed, then either collagenase, kallikrein and/or proline-specific endopeptidase are used to further digest such fraction(s). The Sephadex G-25 chromatography is employed to monitor this further digestion.

Gel Filtration Chromatography

Once the optimal time for digestion and the elution profile of digested protamine on Sephadex G-25 chromatography are established, the process is repeated with unlabelled protamine, since TNBS labels on protamine may interfere with sensor measurements of the heparin-neutralizing activity of LMWP. A solution containing 0.1 M ammonium acetate at pH 7.0 is used as the eluting buffer, since this salt is volatile and easily removed during lyophilization of the samples. The heparin-neutralizing ability of each fraction is measured using the new assay described above. Since in vitro and in vivo studies require large quantity of the compound, fractions possessing the desired, or above the desired heparin-neutralizing activity and without too diverse molecular weights (e.g. within 500 daltons) are pooled and lyophilized for subsequent uses. An aliquot of the LMWP fraction that has the highest heparin-neutralizing ability is reserved for further purification to homogeneity.

LMWH-Affinity Chromatography

Owing to the long polymeric chain and evenly distributed negative charges on the polymer chain, native heparin may bind with all of the ficin-produced LMWP species, large or small, as long as they contain a few arginine residues. Since LMWP fragments that bind to heparin competitively and specifically at the ATIII-binding region are most desired, LMWH can be used as the ligand in affinity chromatography for LMWP. The lower molecular weight of LMWH reduces the possibility for non-specific binding with the smaller arginine-containing species. Preferred for use in particular aspects of the invention is porcine intestinal LMWM from Sigma (St. Louis, Mo.), with an average molecular weight of 3000 daltons (the smallest LMWH species commercially available), although other LMWH species (also available from Sigma) are contemplated for use in other aspects of the invention.

The LMWH is further purified using an ATIII-Sepharose (Sigma) column to remove impurities prior to immobilization. The purified LMWH is immobilized on agarose beads using the cyanogen bromide activation method (Kim and Yang, 1992). To facilitate large scale production, batch chromatographic procedures are adapted. The LMWP preparations obtained above are mixed with adequate amount of the LMWH-agarose beads. The reaction mixture is agitated using an orbital rotator, and the beads are separated from the superiatant by centrifugation. Following the same procedures, the beads are subsequently washed with buffers containing increasing concentrations of NaCl. The washings are collected and dialyzed overnight to remove the salt, using a desalting dialysis membrane with a molecular weight cutoff of 100 daltons (Spectrum Medical Industries, Los Angeles). The dialyzed fractions are lyophilized and then analyzed for heparin-neutralizing activity using the assay procedures described above. LMWP preparations after Sephadex G-25 gel filtration are already of reasonable purity, and thus preparations following this LMWH-affinity approach are significantly purer, if not homogeneous.

At least one, and in certain instances multiple, LMWP fragment with the desired heparin-neutralizing activity is produced from the digestion of a single protamine molecule. An overall recovery yield of at least about 15% for LMWP after purification is obtained. Since gel filtration is conducted with an automated FPLC system and affinity chromatography is performed using batch procedures, this purification scheme is suitable for mass production of LMWP. If a second protease (e.g., collagenase) digestion is required to further degrade the large fragment(s) that are produced in the ficin digestion, then those new LMWP species are subjected to the same gel filtration and LMWH-affinity chromatography to maximize the recovery of desired LMWP species.

B. Homogeneous LMWP Preparation for Sequence Analysis

Gel filtration separates LMVP fragments by their size, whereas affinity chromatography separates them by their charge and specific binding towards LMWH. If the LMWP preparation is still not homogeneous after these two steps of purification, then the remaining difference among such inseparable species is most likely attributed to their peptide configuration. To further purify these species, a purification step based on reverse-phase chromatography is utilized.

The purity of the LMWP preparations, obtained from each purification step and possessing the highest heparin-neutralizing activity, is examined by SDS-PAGE (Yang et al., 1985). If more than one band is present following the LMWH-affinity purification, the preparation is subjected to a FPLC reverse-phase column packed with Zorbax LP-100/40C8 (Sigma) sorbents. This column is capable of further separating the Sephadex G-25 purified, thermolysin-digested LMWP species into 4 different peaks.

The sequence of the desired LMWP allows for the economic production of mass quantities using recombinant DNA techniques. In addition, desired LMWP peptides serve as lead compounds to further design additional potent and non-toxic heparin-neutralizing agents using combinatorial chemistry techniques.

C. In Vitro Studies

In certain aspects, in vitro studies are intended to establish the foundation work for in vivo studies. However, for certain specific investigations, including the antigenicity of LMWP, its aggregatory function on platelet, and its inhibitory effects on thrombin and carboxypeptidase N, in vitro approaches are the only relevant and feasible means to conduct such studies.

1. Antigenicity of LMWP

Human Anti-protamine Antibodies

Figure 7:
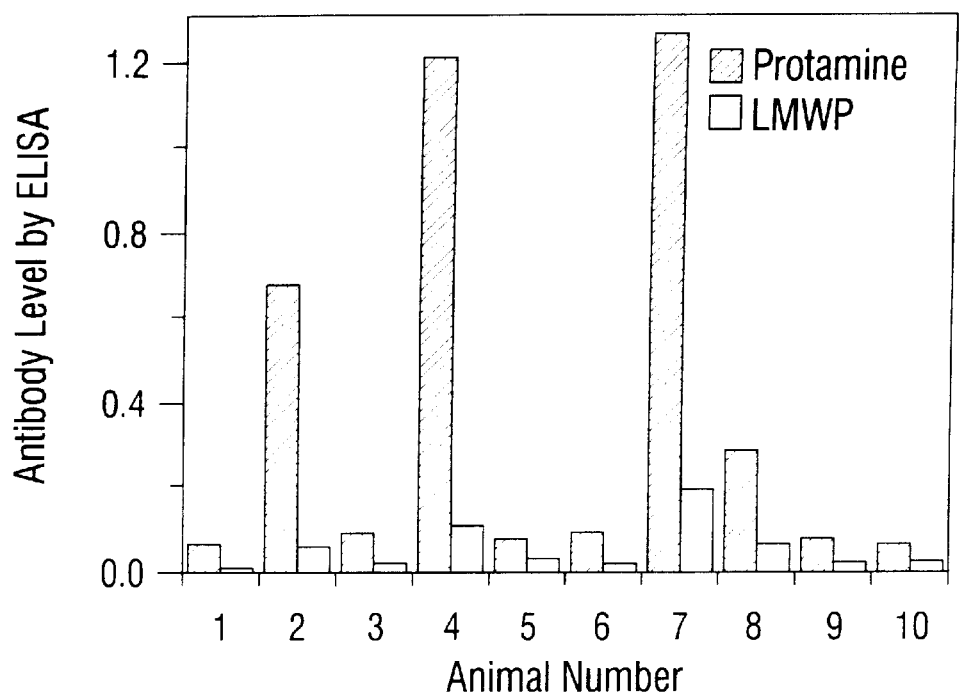
FIG. 7. Detection of protamine antibody and cross-reactivity with LMWP in mice. Production of anti-protamine antibodies (hatched boxes) was measured by the ELISA assay using protamine-coated microplate, whereas the cross-reactivity with LMWP (open boxes) was measured by the same ELISA but using a LMWP-coated plate. Antibody level by ELISA is shown on the vertical axis, and the animal number is shown on the horizontal axis.

LMWP possesses markedly reduced antigenicity (i.e. the ability to be recognized by an antibody) compared to protamine towards mouse anti-protamine antibodies (FIG. 7). To closely mimic the clinical events and assess the real clinical benefits of LMWP, antigenicity is tested against human anti-protamine antibodies. As described previously, among the four groups of patients who have been exposed to protamine and thus potentially have anti-protamine antibodies, diabetic patients represent the largest population and also at the highest risk to protamine response. Indeed, 25–40% of patients with insulin-dependent diabetes mellitus have anti-protamine antibodies in their serum (Nell and Thomas, 1988). Thus, these patient sera are used as a source of protamine antibodies.

Antigenicity Measurements

The sera from diabetic patients are screened for anti-protamine antibodies and positive samples are designated as $APA^+$ (Singh and Tingle, 1982). In brief, protamine or LMWP (5 $\mu$g/well) is used to coat wells of the microplate. After blocking and washing, $APA^+$ human serum is added at three dilutions: 1:50, 1:500, and 1:5000. After an hour of incubation at room temperature, the plate is washed as before. To each well, 100 $\mu$L of goat-antihuman-IgG-alkaline phosphatase (1:1000 dilution) is pipetted. The plate is incubated for 1 h at room temperature. The plate is washed 4 times and 100 $\mu$L of p-nitrophenyl-phosphate solution (1 mg/ml) is added. After 30 min, the absorbance of yellow color is measured at 405 nm using a microplate reader (Bio-Rad Model 3550). Cross-reactivity of human anti-protamine antibodies to commercial protamine is indicated by a positive reaction in this assay using a protamine-coated microplate. Similarly, cross-reactivity and/or antigenicity of LMWP towards human antiprotamine antibodies is measured by the same assay using a LMWP-coated microplate. Comparison of antigenicity and cross-reactivity is made between protamine and LMWP species.

2. Other Toxicity Studies

As discussed previously, a variety of protamine-induced toxicological events, including the activation of the complement system, are attributed to the "bridging" property of protamine. LMWP, with significantly shortened chain length, is reduced or even devoid of such behavior. Several representative and yet key toxicological events that result from the bridging property of protamine are studied.

Inhibition of Carboxypeptidase N

Protamine can block the inactivation of kinins and anaphylatoxins by inhibiting carboxypeptidase N (CPN) (Tan et al., 1989), thereby potentiating these two factors implicated in the catastrophic reaction to protamine administration. This inhibition appears to relate to the binding of protamine to CPN. Thus, the binding of LMWP to CPN as well as its induced inhibition of CPN in the conversion of the kinin substrate is studied. Binding of LMWP to CPN is rapidly and precisely monitored using the protamine sensor (Yun et al., 1993). In the absence of binding, the protamine sensor yields significant potentiometric response to LMWP, whereas in the presence of binding, a linear reduction of the potential in relation to the degree of binding is observed. The binding constants of LMWP and protamine to CPN are determined by the protamine sensor (Yun et al., 1993).

The inhibition of CPN by LMWP is followed by measuring the hydrolysis of bradykinin (Tan et al., 1989). Reaction products are separated and quantitated by HPLC, and the Lineweaver-Burk plot of the inhibition reaction at different doses of LMWP is constructed. For comparison, a parallel study using protamine as the inhibitor for CPN is conducted.

Inhibition of Thrombin

One of the primary reasons that protamine shows anticoagulant properties when used in large doses is due to its inhibition of thrombin. The mechanism of this inhibition is similar to that by ATIII; and is initiated by the binding of protamine to thrombin, followed by the inhibitory effects on thrombin in the conversion of fibrinogen to fibrin. Thus, the binding of LMWP to thrombin as well as its induced inhibition of the catalytic activity of thrombin is studied. The binding of LMWP to thrombin is quantitated using the protamine sensor, whereas inhibition of thrombin activity is measured by a chromagenic assay (Cobel-Geard and Hassouna, 1983) and S-2238 as the substrate. Again, for comparison purpose, a parallel study using protamine as the inhibitor for thrombin is conducted as a control.

Aggregatory Effect on Platelet

The positively charged protamine polymer adheres to the negatively charged platelet membrane, thereby inducing platelet aggregation by the formation of bridges between adjacent platelets (Eika, 1972). To examine the effect of the chain-shortened LMWP on this activity, the induction in platelet aggregation by LMWP is determined (Eika, 1972). In brief, blood samples (in EDTA vacutaniners) from donors are obtained from the American Red Cross. They are centrifuged at 800–1000 rpm for 5 min, and the plasma is decanted as platelet rich plasma (PRP). Platelet counts are done on the PRP samples using a phase-contrast microscopy, so that platelet numbers are standardized for the aggregation test. To 1.8 ml of the PRP suspension, 0.1 ml of 50 mM $CaCl_2$ and 0.1 ml of the solution containing LMWP (at three different concentrations of 0.5, 5, and 2.5 mg/ml) are added. Platelet aggregation is measured using a dual-sample aggregation meter (Model DP-247-E, Sienco, Morrison, Colo.). A parallel set of studies are conducted using protamine as the aggregating agent as a control.

D. In Vivo Studies

In vivo studies are used to study those elements that are important to the promotion of LMWP as a non-toxic therapeutic agent, for example in clinical heparin reversal. These elements include: the efficacy and toxicity of LMWP as a clinical heparin-neutralizing agent, and the immunogenicity and metabolic clearance of this agent during its clinical use.

1. Animal Models

In the study of the efficacy and toxicity of LMWP, the dog is chosen as the animal model. This is because the dog is one of the most economical animal species for this type of acute studies. Most importantly, the dog is known to magnify the typical human responses noted with protamine reversal of heparin (Horrow, 1985). Among a variety of animal species tested, dogs with intravenous injection of protamine display the most outstanding hemodynamic changes (Jaques, 1973; Horrow, 1985). By selecting an animal species that is most vulnerable to protamine response, if LMWP induces only benign or indeed insignificant adverse responses in this species, then it should not pose any threat to the safety in less sensitive species such as human beings.

For all the other studies not involving cardiovascular responses, including the chronic studies to examine the immunogenicity of LMWP and the pharmacokinetics and biodistribution studies of the administered LMWP, mouse and rat models are selected as the respective animal model. Such choices are primarily based on economical considerations.

2. Efficacy and Toxicity of LMWP

Healthy female mongrel dogs, weighing 20 to 30 kg, are used for this study. Animals are anesthetized with 15 mg/kg sodium pentobarbital, intubated, and maintained on positive pressure ventilation with 4 liters/min supplemental oxygen during the study. Hydration is maintained with an intravenous infusion of lactated Ringer's solution, 22 ml/kg/hr. All animals are housed and cared for according to the guidelines of the "Principles of Laboratory Animal Care" (National Society for Medical Research) and "Guide for the Care and Use of Laboratory Animals" (NIH Publication No. 86-23, revised 1985).

All animals receive intravenous injection of normal heparin (100 IU/kg) or LMWH (Enoxaparin; 150 IU anti-Xa activity per gram of body weight), followed 30 min later by administration of either protamine or LMWP. The required doses for protamine and LMWP are determined as described above. When heparin is used as the test anticoagulant, the protamine (or LMWP) dose employed is 1.5 times of that required to fully neutralize the administered aPTT activity. When LMWH is used as the test anticoagulant, the protamine (or LMWP) dose employed is 1.5 times of that required to fully neutralize the administered anti-Xa activity. Protamine or LMWP are given intravenously into a femoral vein over a 10 second period to maximize hemodynamic effects.

Catheters are inserted into the left carotid artery for monitoring systemic mean arterial blood pressure (MAP) and heart rate (HR). An oximetric Swan-Ganz catheter is placed into the pulmonary artery for measurement of pulmonary artery systolic and diastolic pressures (PAS/PAD) and mixed venous oxygen saturation ($S_vO_2$). A catheter is also placed into the femoral artery for monitoring the systemic arterial oxygen saturation ($S_aO_2$). The pulmonary artery flow as a measure of cardiac output (CO) is determined with an electromagnetic square-wave flow probe (Narcomatic, Houston, Tex.). The systemic oxygen consumption ($VO_2$) is calculated from these measurements using the Fick equation relationship:

$$\text{oxygen consumption} = \text{flow} \times \text{hemoglobin} \times 1.34 [S_aO_2 - S_vO_2]$$

All hemodynamic data are collected and assessed with an on-line computer Work-Bench Program (Strawberry Tree, Sunnyvale, Calif.) that allows for continuous monitoring of both measured and calculated hemodynamic parameters.

Unless otherwise stated, data are expressed as mean±SD. Statistical analysis includes linear regression to determine correlation coefficients, analysis of variance (ANOVA), and unpaired two-tailed Student's t test where appropriate (Statworks; Cricket Software, Philadelphia, Pa.). Results are compared between protamine and LMWP against a specific anticoagulant (i.e. heparin or LMWH).

Overall, 48 dogs are used. These dogs are distributed into four groups: [1] 12 dogs are given heparin followed by neutralization with protamine; [2] 12 dogs are given LMWH followed with protamine; [3] 12 dogs are given heparin followed with LMWP; and [4] 12 dogs are given LMWH followed with LMWP. A success rate of 80% for animal studies ensures that the numbers of animals involved in each group should yield statistically meaningful results.

Efficacy

To study the in vivo efficacy of LMWP, coagulation studies are performed in venous blood samples obtained before heparin (or LMWH) administration, 3 min before neutralization, and at 3, 10, and 30 min after the neutralization with protamine (or LMWP). These studies include determination of activated clotting time (ACT), thrombin clotting time (TCT), prothrombin time (PT), activated partial thromboplastin time (aPTT), anti-Xa activity, and anti-IIa activity. ACT measurements are made using a Hemochron (International Technidyne, Edison, N.J.) immediately on blood withdrawn with 2 ml whole blood and celite-containing tubes. The remainder of the blood is placed into standard citrated tubes and either stored on ice for anti-Xa or anti-IIa determinations or spun down at 900 rpm for 10 min to obtain platelet-rich plasma (PRP). Prothrombin times and aPTT are performed on 0.1 ml PRP with commercially available prothrombin time and GPC cartridges, respectively (HemoTec, Parker, Colo.). The aPTT test is activated by addition of 0.1 ml rabbit cephaloplastin (Baxter, Miami, Fla.). The TCT test is performed on a Fibrosystem (Becton-Dickinson, Cockeysville, Md.), using 0.2 ml PRP and 0.1 ml TCT reagent (American Dade, Miami, Fla.). The anti-Xa and anti-IIa activity are determined by the Coatest chromogenic assay (Kabi Vitrum, Stockholm, Sweden) using S-2222 and S-2238 as the chromogenic substrates, respectively (Yang et al., 1986). All tests are performed in triplicate.

Toxicity

The in vivo toxic effects of protamine are best manifested by its induced hemodynamic responses. Other phenomena, such as hematological responses (e.g. thrombocytopenia), complement activation, and the release of histamine and/or thromboxane can also serve as an index for assessing protamine-induced adverse responses. All these parameters are monitored during the studies in the canine model.

a. Hemodynamic Responses

Hemodynamic parameters include mean arterial blood pressure (MAP), heart rate (HR), pulmonary artery systolic/diastolic pressures (PAS/PAD), mixed venous oxygen saturation ($S_vO_2$), cardiac output (CO), and oxygen consumption ($VO_2$). Measurements and calculations are made at baseline, before the administration of heparin (or LMWU), 3 min before neutralization, every 10 sec for 5 min after neutralization, and at 10, 20, and 30 min after neutralization with protamine (or LMWP).

The total toxicity score (TTS) is adapted to assess the toxicity for protamine and LMWP (Wakefield et al., 1994; Wakefield et al., 1996). In brief., the TTS, which includes the maximum change in MAP, CO, $VO_2$, and HR during the first 5 min after heparin (or LMWH) neutralization, is calculated for each protamine and LMWP. The maximum changes that occurs in the individual dog is divided by the standard deviation derived from the entire group of animals in all group combined and then the scores are added to compute the WTS for each individual dog. In each group, the mean of the scores is then calculated to obtain a TTS for each protamine and LMWP against either heparin or LMWH. The more negative the value (against the same anticoagulant), the more toxic the neutralizing agent during the reversal of the specific anticoagulant.

b. Hematological Effects

The use of protamine for heparin reversal induces thrombocytopenic responses (Horrow, 1985). Additionally, transient granulocytopenia is manifested in patients undergoing protamine treatment (Horrow, 1985; Jacob et al., 1980). To compare the hematological effects between protamine and LMWP, platelet count and white blood cell count are determined. Platelet and white blood cell counts are analyzed by hand hemocytometry methods with a diluted red blood cell lysis method (Unopette, Becton-Dickinson).

In studies of complement activation by heparin-protamine complexes (HPC), the lymphocyte count was reduced by about 50% in rabbits 5 min after protamine administration, suggesting that HPC interacted with lymphocyte (Fehr and Rohr, 1983). To determine if LMWP is immunotoxic, a lymphocyte count is taken microscopically after staining with crystal violet. A reduction in lymphocyte count is an indication of the immunotoxicity of the compound. As in the studies described below, blood samples are drawn at 3 min before neutralization, and at 0, 5, 10, 20, and 30 min after neutralization with protamine (or LMWP).

c. Complement Activation

The majority of the non-immunological-mediated adverse responses to protamine are triggered either directly or indirectly by complement activation. Thus measurements of complement activation provide one of the most reliable sources of information in assessing protamine toxicity. The lack of commercial antibodies against any of the complement components in the dog limits the studies to only a few available assays. A combination of these in vivo studies with the in vitro studies described above provide sufficient data with regard to the difference in complement activation by the two protamine species (i.e. protamine and LMWP).

Similar to the in vitro studies, complement activation is first determined by assaying plasma samples for total hemolytic complement activity ($CH_{50}$ units; Yang et al., 1991b; Yang et al., 1991a). Secondly, effects of the drugs on the complement system are monitored on polymorphonuclear (PMN) cell count and C-reactive protein (CRP) level. These parameters significantly change due to acute intravascular complement activation following heparin/protamine administration (Fehr and Rohr, 1983; Claus et al., 1977). PMN are counted using a Coulter Model S counter (Coulter Electronics, Inc., Hialeah, Fla.). CRP is quantitated by microplate-ELISA (Singh and Tingle, 1982). Thirdly, complement activation is studied by measuring the plasma C3 levels (Wakefield et al., 1988). The C3 levels are determined by the crossed immunoelectrophoresis method (Mancini et al., 1965), using a specific antibody against canine C3. Since the height of the C3 peak in the gel slab relates directly to the amounts of C3 present in plasma, percentage changes in C3 concentrations are readily calculated.

d. Histamine Release

A possible mechanism for transient hypotension associated with the rapid infusion of protamine for heparin reversal is the release of histamine due to the degranulation of mast cells (Horrow, 1985; Weiler et al., 1985; Sander and Hirshman, 1990). Prophylactic injection of histamine receptor blockers has been shown to prevent protamine related hemodynamic effects (Kambam et al., 1990). Thus measurement of blood histamine levels serve as a specific marker to indirectly assess the toxicity of protamine and LMWP. Plasma histamine levels are determined at the aforementioned time intervals, using a radioenzymatic assay (Bowsher et al., 1983).

e. Thromboxane Release

Several parameters such as complement activation and thromboxane generation have been demonstrated to be most responsible for acute manifestations observed during protamine neutralization of heparin (Morel et al., 1990; Lowenstein and Zapol, 1987; Weiler et al., 1985). Measurement of thromboxane release, therefore, is used as another index to compare the toxicity between protamine and LMWP. Plasma thromboxane $B_2$ ($TxB_2$) levels are determined by a standard radioimmunoassay using a commercial $TxB_2$ kit (Amersham International, Buckinghamshire, UK) with a sensitivity of <2 pg/100 μl plasma.

f. Heparin Rebound

One of the causes of excessive bleeding after the use of extracorporeal bypass procedures is the so-called "heparin rebound". The heparin rebound phenomenon, wherein heparin activity recurs in the circulation following protamine administration to heparinized patient, has been reported in many clinical cases (Ellison et al., 1974). Several hypotheses (Ellison et al., 1974; Shanberge et al., 1987; Fabian and Aronson, 1980) have been proposed to explain this phenomenon, of which one seems more convincing. This mechanism suggests that a metabolic removal of protamine takes place that somehow elicits the reappearance of heparin in the circulation (Fabian and Aronson, 1980).

Since LMWP, produced by enzymatic digestion of native protamine, may possess altered pharmacokinetics and metabolic clearance, the heparin rebound phenomenon is studied following neutralization of heparin with the two protamine species. Blood samples are drawn immediately upon the conclusion of the in vivo efficacy/toxicity studies, and also at 15, 30 60, and 120 min after the study. The sample drawn at the conclusion of the study serves as a control. The blood clotting time in these samples is measured by the aPTT and ACT assays. The results of utilizing protamine and LMWP as the neutralizing agent are compared.

3. Immunogenicity Studies

As shown herein, anti-protamine antibodies were successfully produced in four out of ten mice tested (FIG. 7). None of the five mice administered LMWP showed signs of producing antibodies. To further verify these results, large scale immunogenicity studies are conducted. A total of 20 mice are used to test each protamine species. Since every study is a chronic study that will last for at least one month, 25 mice are prepared for each test protamine species, assuming a survival rate of 80% for the mice over a 40 day period. Overall, 50 mice are required.

Production of Antibodies

Polyclonal antibodies to protamine and LMWP are developed in mice (Cooper and Paterson, 1991). Briefly, mice are bled before immunization for pre-immune sera. They are injected intradermally with 100 μl of the protamine species (50 μg) mixed with complete Freund's adjuvant (CFA) (Sigma). After 4 wk, mice are bled, and the first booster is given with 5 μg of LMWP in incomplete Freund's adjuvant (IFA). Second and third booster immunizations are given at two-wk intervals. Afterwards, mice are bled for immune sera. Blood is drawn from the tail vein and, after clotting for 30 min at room temperature, is centrifuged at 1,500×g for 5 min for serum collection.

Assay for Antibodies

The antibodies produced are detected by enzyme linked immunosorbent assay (ELISA) (Singh and Tingle, 1982). Briefly, 100 μl of 50 μg/ml solution of the related protamine species are pipetted into microwells of a 96-well microplate (Corning). After coating of the antigen (16 to 18 h at 5° C.), the microwells are washed 4 times with PBS (0.01 M sodium phosphate, 0.15 M NaCl, pH 7.4) containing 0.1% Tween 20. Blocking is done with 1% bovine serum albumin (BSA). Pre-immune or immune sera, prediluted to 1:50, 1:500 and 1:5000 dilutions, is pipetted in triplicate wells. After 1 h of incubation at room temperature, the wells are washed 4 times. To each well, 100 μl of goat-antimouse-IgG-alkaline phosphatase solution (1:1000 dilution) are pipetted and the plate is incubated for 1 h at room temperature. The plate is washed 4 times again and 100 μl of p-nitrophenylphosphate solution (1 mg/ml) are added to each well. After 30 min, the absorbance of yellow color is read at 405 nm using a Microplate Reader (Bio-Rad Model 3550). Increase of optical density above blank (without serum) or pre-immune serum demonstrates the presence of antibodies in the immune serum.

Antigenicity/Cross-Reactivity

Although the in vitro studies utilizing human anti-protamine antibodies from diabetic patients yield the most relevant and conclusive information about the antigenicity and cross-reactivity of LMWP, these properties are also examined using in vivo studies for comparison purpose. In brief, serum samples from the protamine-immunized mice with clear identification of the presence of anti-protamine antibodies are examined with the same ELISA assay using a LMWP-coated microplate as described above. The detection of an absorbance reading at 405 nm indicates the presence of antigenicity and cross-reactivity of LMWP toward anti-protamine antibodies.

4. Pharmacokinetics/Biodistribution

For any therapeutic drug to be considered for potential clinical use, information about its pharmacokinetics and biodistribution must be determined. Although LMWP is small peptide derived enzymatically from a clinically approved drug (i.e. protamine), this modification process could result in altered pharmacokinetics of the drug, such as clearance, metabolism, excretion, and tissue distribution. Thus, the pharmacokinetics and biodistribution of LMWP are studied. In general, small peptides normally enjoy enhanced bioavailability and compatibility.

To facilitate the monitoring process, radiolabeled materials are used for the studies. Radio-iodination is performed on the both protamine and LMWP, using the chloramine-T method (Hunter and Greenwood, 1962). This method yields a low degree of iodination but a high degree of specific activity, thereby running little risk of affecting the structure or activity of the labeled proteins. Indeed, this method has been employed to label a variety of proteins and enzymes for clearance studies without revealing untoward effects (Cook et al., 1992; Runge et al., 1987).

Pharmacokinetic Studies

Sprague-Dawley rats (300 g) are used for the studies. The right jugular vein is cannulated with silicone rubber-polyethylene cannula (0.037 inch o.d.) (Weeks and Davis, 1964). This shunt is used for sample injection and blood collection. Six groups are established including: the intravenous administration of [1] protamine alone; [2] LMWP alone; [3] 300 IOU of heparin, and 5 min later followed by protamine; [4] same as [3] but followed by LMWP; [5] 300 U of anti-Xa activity of LMWH, and 5 min later followed by protamine; and [6] same as [5] but followed by LMWP. The $^{125}$I-labeled test protamine species is infused over 5 min at three doses (2, 5, and 10 mg) to the rat via the shunt. These three protamine doses ensure that at least one dose will be below and one dose will be above that required for a full heparin neutralization. Blood samples (0.25 ml) are drawn to syringes containing citrate at 5, 10, 15, 20, 30, 45, 60 min, and every 0.5 h thereafter until 5 h after the injection. The blood is centrifuged immediately and the plasma is frozen at <20° C. until subsequent analysis. The first sample taken 30 sec after injection is designated as that which contains 100% of the total plasma radioactivity. Radioactivity of samples is measured and the percentage of label remaining in the circulation is calculated by dividing the cpm of the subsequent sample by the cpm of the initial sample. Five rats are used for each dose regimen, and overall 90 rats are planned for the entire pharmacokinetic studies of the six test groups.

The data describing the disappearance of the test compounds are fitted with sum of two exponential (exp) terms: $C(t)=R\exp(-\alpha t)+S\exp(-\beta t)$. The coefficients (R and S) and exponents ($\alpha$ and $\beta$) of this function are obtained from semilogarithmic plots by graphic curve peeling performed as follows. The curve for the terminal phase of the plasma radioactivity plotted against time is fitted with a straight line yielding the ordinate intercept S and the slope-$\beta$. The extrapolated values are subtracted from the values obtained during the initial phase, and these data are fitted with a straight line yield the intercept R and the slope-$\alpha$. The disappearance of the test compound is represented by a two compartment mammillary model (Berman and Schoenfeld, 1956) composed of one central and one peripheral compartment with elimination occurring from the central compartment.

Pharmacokinetic parameters are calculated from these coefficients and exponents with standard formulas derived by Gibaldi and Perrier (1983). The variables A and B are first calculated, assuming steady state at the end of the infusion, using the formulas $A=RX_o^\alpha/k_o$ and $B=SX_o/k_o$, where $X_o$ is total administered dose, and $k_o$ is the rate of infusion. From these constants, the following drug disposition parameters are derived: (i) volume of the central compartment $(V_c)=X_o$(A+B); (ii) extrapolated area under the curve $(AUC)=A/\alpha+B/\beta$; and (iii) plasma clearance $(Cl_p)=X_o/AUC$.

Biodistribution Studies

Immediately following the clearance studies, the rats are sacrificed. The animals are shaved and the following organs are removed: brain, lung, heart, kidney, liver, spleen, stomach, and spleen. The organs are homogenized and treated (Larsen et al., 1984), and the homogenate is then be assayed for radioactivity.

Additional studies are performed on rats to examine the long-term (i.e. 24 h and 7 days) tissue distribution of the protamine species. The rats and 6 test groups are prepared the same way as described above, and only one dose (5 mg) of the $^{125}$I-labeled protamine species is administered. The animals are placed in Nalgene metabolic cages (Nalge Co., Rochester, N.Y.), which effectively separate the urine. At time intervals of 24 h and 7 days, the animals are sacrificed, and the urine, blood and the above organs are collected and assayed for radioactivity. Each experimental group and each time interval (i.e. 24 h or 7 days) consists of 5 rats, and overall 60 rats are used for the entire long-term studies.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods, and in the steps or in the sequence of steps of the methods described herein, without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adkins and Hardy, "Sodium heparin neutralization and the anticoagulant effects of protamine sulfate," *Arch. Surg.*, 94:175–183, 1967.

Adourian, Hirshman, Adkinson, Weiss, Immunoactivity of protamine preparations used to reverse heparin anticoagulation, *Anesthesiology*, 73:328–331, 1990.

Adourian, Shampaine, Hirshman, Fuchs, Adkinson, "High-titer protamine-specific IgG antibody associated with anaphylaxis: report of a case and quantitative analysis of antibody in vasectomized men," *Anesthesiology*, 78:368–372, 1993.

Ando, Yamsaki, Suzuki, "Protamine,". In: *Molecular Biology Biochemistry and Biophysics*, Kleinzeller A, ed., Vol. 12, pp 1–109, Springer-Verlag, N.Y., 1973.

Berman and Schoenfeld, "Invariants in experimental data on linear kinetics and the formulation of models," *J. Appl. Physiol.*, 27:1361–1370, 1956.

Bourin and Lindahl, "Glycosaminoglycans and the regulation of blood coagulation," *BioChem., J.*, 289:313–330, 1993.

Bowsher, Verburg, Henry, "Rat histamine-N-methyl transferase quantitation, purification, and immunologic properties," *J. Biol. Chem.*, 258:12215–12220, 1983.

Bradford, "A rapid and sensitive method for the quantitation of microgram quantities of protein utilizing the principle of protein-dye binding," *Anal. Biochem.*, 72:248–254, 1976.

Byun, Wang, Kim, Yang, "Optimization and assessment of the in vitro efficacy of a heparin-removing bioreactor using mathematical modeling," *J. ASAIO*, 42:782–787, 1996.

Cardin and Weintraub, "Molecular modeling of protein-glycosaminoglycan interactions," *Arteriosclerosis*, 9:21–32, 1989.

Casu, "Structure of heparins and their fragments," *Nouv. Rev. Fr. Hematol.*, 26:211–219, 1984.

Casu, Oreste, Torri et al., "The structure of heparin oligosaccharide fragments with high anti-Xa activity containing the minimal antithrombin III-binding sequence," *Biochem. J.*, 197:599–609, 1981.

Cavarocchi, Schaff, Homburge, Schnell, "Evidence for complement activation by protamine-heparin interaction after cardiopulmonary bypass," *Surgery*, 98:525–531, 1985.

Choay, Lormeau, Petitou, Sinay, Fareed, "Structure studies on a biologically active hexasaccharide obtained from heparin," *Ann. NY Acad. Sci.*, 370:644–649, 1981.

Claus, Siegel, Petras, Skor, Osmand, Gewurz, "Complement activation by interaction of polyanions and polycations III: Complement activation by interaction of multiple polyanions and polycations in the presence of C-reactive protein," *J. Immunol.*, 118:83–87, 1977.

Click, Homburger, Bove, "Complement activation from protamine sulfate administration after coronary angiography," *Cathet. Cardiovasc. Diagn.*, 16:221–225, 1989.

Cobb III and Fung, "Shock due to protamine hypersensitivity," *Surg. Neurol.*, 17:245–246, 1982.

Cobel-Geard and Hassouna, "Interaction of protamine sulfate with thrombin," *Am. J. Hematol.*, 14:227–233, 1983.

Conzen, Habazettl, Gutmann, et al., "Thromboxane mediation of pulmonary hemodynamic responses after neutralization of heparin by protamine in pigs," *Anesth. Analg.*, 68:25–31, 1989.

Cook, Niewiarowski, Yan et al., "Platelet factor 4 efficiently reverses heparin anticoagulation in the rat without adverse effects of heparin-protamine complexes," *Circulation*, 85:1102–1109, 1992.

Cooper and Paterson, "Production of antibodies," In: *Current Protocols in Immunology*, Coligan, Kruisbbek, Margulies et al. (eds.), Section 2.4.1–2.4.7, Green Publishing Associates and Weley-Interscience, New York, 1991.

Cormack and Levy, "Adverse reactions to protamine," *Coron. Artery Dis.*, 4:420–425, 1993.

Diness and Ostergaard P B: Neutralization of low molecular weight heparin (LHN-1) and conventional heparin by protamine sulfate in rats," *Thromb Haemost* 56:318–322, 1986.

Dykewicz, Kim, Orfan, Yoo, Lieberman, "Immunologic analysis of anaphylaxis to protamine component in neutral protamine Hagedom human insulin," *J. Allergy Clin. Immunol.*, 93:117–125, 1994.

Ellison, Beatty, Blake, Wurzel, MacVaugh III, "Heparin rebound studies in patients and volunteers," *J. Thorac. Cardiovas. Surg.*, 67:723–729, 1974.

*Enzyme Nomenclature*. Published for the International Union of Biochemistry by Academic Press, Inc., New York, 1984.

Erdos, "Enzymes that inactivate polypeptides," In: *Metabolic Factors Controlling Duration of Drug Action*, Bordie and Erdos (eds), pp159–178, Pergamon Press, Oxford, 1962.

Erika, "On the mechanism of platelet aggregation induced by heparin, protamine and polybrene," *Scand. J. Haemat.*, 9:248–257, 1972

Fabian and Aronson, "Mechanism of heparin rebound: In vitro study," *Thromb. Res.*, 18:535–542, 1980.

Fehr and Rohr, "In vivo complement activation by polyanion-polycation complexes: evidence that C5a is generated intravascularly during heparin-protamine interaction," *Clin. Immunol. Immunopathol.*, 29:7–14, 1983.

Gallop, Barrett, Dower, Fodor, Gordon, "Applications of combinatorial technologies to drug discovery 1: background and peptide combinatorial libraries," *J. Med. Chem.*, 37:1233–1251, 1994.

Gibaldi and Perrier *Pharmacokinetics*, pp 45–111, Marcel Dekker, Inc., New York, 1983.

Gordon, Barrett, Dower, Fodor, Gallop, "Applications of combinatorial technologies to drug discovery 2: combinatorial organic synthesis, library screening strategies, and future directions," *J. Med. Chem.*, 37:1385–1401, 1994.

Gottchlich, Gravlee, Georgitis, "Adverse reactions to protamine sulfate during cardiac surgery in diabetic and nondiabetic patients," *Ann. Allergy*, 61:277–281, 1988.

Gottschlich and Georgitis, "Protamine-specific IgE, IgG, and IgG subclass antibodies in protamine anaphylaxis," *J. Allergy Clin. Immunol.*, 81 (Abs):238, 1988.

Griffith, "Heparin-catalyzed inhibitor/protease reactions: kinetic evidence for a common mechanism of action of heparin," *Proc. Natl. Acad. Sci. USA*, 80:5460–5464, 1983.

Gupta, Veith, Ascer et al., "Anaphylactoid reactions to protamine: an often lethal complications in insulin-dependent diabetic patients undergoing vascular surgery," *J. Vasc. Surg.*, 9:342–350, 1989.

Harenberg, Gnasso, de Vries, Zimmermann, Augustin, "Inhibition of low molecular weight heparin by protamine chloride in vivo," *Thromb. Res.*, 38:11–20, 1985.

"Hemostasis and Thrombosis," In: *Pharmacology*, Rang H P, Dale M M, Ritter J M, Gardner P, eds, pp 331–350, Churchill Livingstone Inc., New York, 1995.

Hirchboeck, Madison, Pisciotta, "Alopecia and other toxic effects of heparin and synthetic heparinoid," *Am. J. Med. Sci.*, 227:279–282, 1954.

Hird, Wakefield, Mukherjee, et al., "Direct effects of protamine sulfate on myocyte contractile processes," *Circulation*, 92(11):433–446, 1995.

Hirsh, "Heparin induced bleeding," *Nouv. Rev. Fr. Hematol.*, 26:262–266, 1984.

Holmer, Soderberg, Bergqvist, Lindahl, "Heparin and its low molecular weight derivatives: anticoagulation and antithromboticproperties, *Haemostasis*, 16:1–7, 1986.

Horrow, "Protamine allergy," *J. Cardiothorac. Anesth.*, 2:225–242, 1988.

Horrow, "Protamine: a review of its toxicity," *Anesth. Analg.*, 64:348–361, 1985.

Howell, "Heparin, an anticoagulant: preliminary communication., *Am. J. Physiol.*, 63:434–435, 1922.

Hugli "The structural basis for anaphylatoxin and chemotactic functions of C3a, C4a, and C5a," In: *Critical Reviews in Immunology*, Atassi (ed), pp321–366, Chemical Rubber, Boca Raton, Fla., 1981.

Hull, Raskob, Pineo et al, "Subcutaneous low-molecular weight heparin compared with continuous intravenous heparin in the treatment of proximal-vein thrombosis," *N. Eng. J. Med.*, 326:975–982, 1992.

Hunter and Greenwood, "Preparation of iodine-131 labeled human growth hormone of high specific activity," *Nature*, 194:495496, 1962.

Hurby, Skrovina, Vanek, "Anaphylactic reaction to protamine in cardiovascular surgery (in Czech)," *Rozhl Chir.*, 74:282–283, 1995.

Insulins. In: *American Hospital Formulary Service (AHFS) Drug Information*, pp 1725–1736, American Society of Hospital Pharmacists, Inc., Bethesda, Md., 1989.

Jacob, Craddock, Hammersmidt, Moldow, "Complement-induced granulocyte aggregation," *N. Engl. J. Med.*, 302:789–794, 1980.

Jaques, "Heparin: Anionic polyelectrolyte drugs," *Pharmacol. Rev*, 31:99–166, 1980.

Jaques, "Protamine: Antagonist to heparin," *Can. Med. Assoc. J.*, 108:1291–1297, 1973.

Jensen and Ens, "Clinical usage of low molecular weight heparin," *Clin Hemostat Rev* Vol. 7, No. 6, pp 1–4, 1993.

Just-Viera, Fischer, Gago, Morris, "Acute reaction to protamine: Its importance to surgeons," *Am. Surg.*, 50:52–60, 1984.

Kambam, Meszaros, Merill, Stewart, Smith, Bender, "Prophylactic administration of histamine and histamine receptor blockers in the prevention of protamine related hemodynamic effects," *J. Canc. Anaesth.*, 37:420–422, 1990.

Katz, Kim, Siegelman, Ved, Ahmed, Wallace, "Hemodynamics of protamine administration," *J. Thorac. Cardiovasc. Surg.*, 94:881–886, 1987.

Kelton and Hirsh, "Bleeding associated with antithrombotic therapy," *Semin. Hematol.*, 17:375–379, 1984.

Kim and Yang, "Protamine immobilization and heparin adsorption on the protamine-bound cellulose fiber membrane," *Biotehcol. Bioeng.*, 39:450–456, 1992.

Kirklin, Chenoweth, Naftel et al., "Effects of protamine administration after cardiopulmonary bypass on complement, blood elements, and the hemodynamic state," *Ann. Thorac., Surg.*, 41:193–199, 1986.

Kitani, Nagarajan, Shanberge, "Effect of protamine on heparin-antithrombin III complexes: In vitro studies," *Thromb. Res.*, 17:367–374, 1980.

Kortt, Hinds, Zerner, "On the specificity and pH dependency of ficin-catalyzed hydrolyses: some comparisons with bromelain specificty," *Biochemistry*, 13:2029–2037, 1974.

Kresowik, Wakefield, Fessler, Stanley, "Anticoagulant effects of protamine sulfate in a canine model," *J. Surg. Res.*, 45:14, 1988.

Kuitunen, Salmenpera, Heinonen, Rasi, Myllyla, "Heparin rebound: a comparative study of protamine chloride and protamine sulfate in patients undergoing coronary artery bypass surgery," *J. Cardiothorac. Vasc. Anesth.*, 5:221–226, 1991.

Kurusz, 6*th Annual Meeting of Pathophysiology and Extracorporeal Technology*, San Diego, Calif., 1986.

Laemmli, "Cleavage of structural proteins during the assembly of the head of bacteriophage T4," *Nature*, 227:680–685, 1970.

Larsen, Hetelekidis, Langer, Disposition and anticoagulant activity of biologically active heparin fragments in rat," *J. Pharmacol. Exp. Ther.*, 231:373–378, 1984.

Lechner, Eichler, Kyrle, "Studies on the neutralizing effects of protamine on unfractionated and low molecular weight heparin (Fragmin) at the site of activation of the coagulation system in man," *Thromb. Haemost.*, 73:439–443, 1995.

Lerner, "Antibodies of predetermined specificity in biology and medicine," In: *Advances in Immunology*, Dixon (ed.), 36:1–44, Academic Press, Inc., NY, 1984.

Levin and Hirsh, 1986 "Hemorrhagic complications of anticoagulant therapy," *Semin. Thromb. Hemostat.*, 12:39–57, 1986.

Levinson and Ohm, "The pathophysiology and treatment of severe protamine reactions in cardiovascular surgery," In: *The Heart Surgery Forum on Internet: message@hsforum.com.*, Jun. 3, 1995.

Liener and Friedenson, "Ficin," *Methods Enzymol.*, 19:261–273, 1970.

Lindahl, Backstrom, Hook, Thunberg, LaFransson, Linker, "Structure of the antithrombin-binding site in heparin," *Proc. Natl. Acad. Sci. USA*, 76:3198–3202, 1979.

Lindblad, "Protamine sulfate: a review of its effects: hypersensitivity and toxicity," *Eur. J. Vasc. Surg.*, 3:195–201, 1989.

Linhardt, "Heparin: An important drug enters its seven decade," *Chemistry and Industry*, pp 45–50, Jan. 21, 1991.

Lowenstein and Zapol, "Protamine reactions, explosive mediator release, and pulmonary vasoconstriction," *Anesthesiology*, 73:373–374, 1990.

Lowenstein, Johnston, Lappas et al., "Catastrophic pulmonary vasoconstriction associated with protamine reversal of heparin," *Anesthesiology*, 59:470–473, 1983.

Ma, Fu, Meyerhoff, Yang, "Electrochemical sensor for heparin: Further characterization and bioanalytical applications," *Anal. Chem.*, 65:2078–2084, 1993.

Ma, Meyerhoff, Yang, "Heparin-Responsive electrochemical sensor: a preliminary study," *Anal. Chem.*, 64:694–697, 1992.

Ma, Meyerhoff, Yang, "Polymer-Based systems for heparin monitoring and removal," *Polymer News*, 19:38–48, 1994.

Majerus, Broze, Miletich, Tollefsen, "Anticoagulant, thrombolytic, and antiplatelet drugs, In: *Goodman and Gilman's "The Pharmacological Basis of Therapeutics"*, 9th edition, pp 1341–1359, 1996.

Mancini, Carbonara, Heremans, "Immunochemical quantitation of antigens by radial immunodiffusion," *Immunochemistry*, 2:235–254, 1965.

Metz and Horrow, "Protamine and newer heparin antagonists," In: *Pharmacology and Physiology in Anesthetic Practice*, Stoelting (ed.), 1(3):1–15, 1994.

Morel, Costabella, Pittet, "Adverse cardiopulmonary effects and increased plasma thromboxane concentrations following the neutralization of heparin with protamine in awake sheep are infusion rate-dependent," *Anesthesiology*, 73:415–424, 1990

Morel, Zapol, Thomas et al., "C5a and thromboxane generation associated with pulmonary vaso- and bronchoconstriction during protamine reversal of heparin," *Anesthesiology*, 60:597–604, 1987.

Neidhart, Meier, Polla, Schifferli, Morel, "Fatal anaphylactoid response to protamine after percutaneous transluminal coronary angioplasty," *Eur. Heart J.*, 13:856–858, 1992.

Nell and Thomas, "Frequency and specificity of protamine antibodies in diabetic and control subjects," *Diabetes*, 37:172–176, 1988.

Okajima, Kanayama, Maeda, et al., "Studies on the neutralizing mechanism of antithrombin activity of heparin by protamine," *Throm. Res.*, 24:21–29, 1981.

Olinger, Becker, Bonchek, "Noncardiogenic pulmonary edema and peripheral vascular collapse following cardiopulmonary bypass: rare protamine reaction?" *Ann. Thorac. Surg.*, 29:20–25, 1980.

Ovrum, Lindberg, Holen, Abdelnoor, "Hemodynamic effects of intraaortic vs intravenous protamine administration after cardiopulmonary bypass in man," *Scand. J. Thorac. Cardiovas.c Surg.*, 26:113–118, 1992.

Park, Pancrazio, Lynch III, "Mechanical and electropysiological effects of protamine on isolated ventricular myocardium: evidence for calcium overload," *Cardiovas Res.*, 28:505–514, 1994.

Porter and Jick, "Drug-Related deaths among medical inpatients," *JAMA*, 237:879–881, 1977.

"Protamine Sulfate," In: *American Hospital Formulary Service (AHFS) Drug Information*, pp 711–713, American Society of Hospital Pharmacists, Inc., Bethesda, Md., 1989.

Rent, Ertel, Eisenstein, Gewurz, "Complement activation by interaction of polyanions and polycations, I. Heparin-protamine induced consumption of complement," *J. Immunol.*, 114:120–124, 1975.

Rosenberg and Lam, "Correlation between structure and function of heparin," *Proc. Natl. Acad. Sci. USA*, 75:1218–1222, 1979.

Rosenberg, "The heparin-antithrombin system: A natural anticoagulant mechanism," In: *Hemostasis and Thrombosis: Basic Principles and Clinical Practice*, Colman, Marder, Hirsh (eds.), 2nd edition, pp 1373–1392, J. B. Lippincott, Philadelphia, 1987.

Runge, Bode, Matsueda, Haber, "Antibody-enhanced thrombolysis: targeting of tissue plasminogen activator in vivo," *Proc. Natl. Acad. Sci. USA*, 84:7659–7662, 1987.

Ryn-McKenna, Cai, Ofosu, Hirsh, Buchanan, "Neutralization of enoxaparine-induced bleeding by protamine sulfate," *Thromb. Haemost.*, 63:271–174, 1990.

Samuel, Kolk, Rumke, "Studies on the immunogenicity of protamine in humans and experimental animals by means of a micro-complement fixation test," *Clin. Exp. Immunol.*, 33:252–260, 1978a.

Samuel, Linnet, Rumke, "Post-vasectomy autoimmunity to protamines in relation to the formation of granulomas and sperm agglutinating antibodies," *Clin. Exp. Immunol.*, 33:261–269, 1978b.

Sander and Hirshman "Protamine-induced histamine release in human skin mast cells," *Anesthesiology*, 73:165–167, 1990.

Sela, "Antigenicity: some molecular aspects," *Science*, 166:1365–1374, 1969.

Shanberge, Murato, Quattrociocchi-Longe, Neste, "Heparin-Protamine complexes in the production of heparin rebound and other complications of extracorporeal bypass procedures," *Am. J. Clin. Pathol.*, 87:210–217, 1987.

Sharath, Metzger, Richerson et al., "Protamine induced fatal anaphylaxis," *J. Thorac. Cardiovasc. Surg.*, 90:86–90, 1985.

Singh and Tingle, "Detection of circulating immune complexes by C1q-microplate ELISA system," *J. Immunol. Methods*, 50:109–114, 1982.

Smith and Kanuer, "A heparin binding site in antithrombin III," *J. Biol. Chem.*, 25:11964–11972, 1987.

Suzuki and Ando, "Studies on protamine XIII: The fraction of clupein Y," *J. BioChem.*, 63:701–708, 1968.

Swartz and Port, "Preventing hemorrhage in high risk hemodialysis: regional versus low total dose heparin," *Kidney Int.*, 16:513–518, 1979.

Tan, Jackman, Skidgel, Zsigmond, Erdos, "Protamine inhibits plasma carboxypeptidase N, the inactivator of anaphylatoxins and kinins," *Anesthesiology*, 70:267–275, 1989.

Verstraete, 1990 "Heparin," In: *Cardiovascular Drug Therapy*, (Messerli F H, ed), pp 1457–1469, W. B. Saunders, Philadelphia, 1990.

Vincent, Janowski, Menlove, "Protamine allergy reactions during cardiac catheterization and cardiac surgery: risk in patients taking protamine-insulin preparations," *Cathet. Cardiovasc. Diagn.*, 23:164–168, 1991.

Wahr, Yun, Yang, Lee, Fu, Meyerhoff, "A new method of measuring heparin levels in whole blood by protamine titration utilizing a heparin-responsive electrochemical sensor," *J. Cardiothorac. Vasc. Anesth.*, 10:447–450, 1996.

Wakefield, Andrews, Wrobleski et al., "A [+18RGD] protamine-varient for nontoxic and effective reversal of heparin and low molecular weight heparin anticoagulation," *J. Surg. Res.*, 63:280–286, 1996.

Wakefield, Andrews, Wrobleski, et al., "Reversal of low molecular weight heparin anticoagulation by synthetic protamine analogues," *J. Surg. Res.*, 56:586–593, 1994.

Wakefield, Till, Lindblad, Saenz, Stanley, Complement depletion and persistent hemodynamic-hematologic response in protamine-heparin reactions," *J. Surg. Res.*, 45:320–326, 1988.

Wakefield, Wrobleski, Nichol, Kadell, Stanley, "Heparin-mediated reductions of the toxic effects of protamine sulfate on rabbit myocardium," *J. Vasc. Surg.*, 16:47–53, 1992.

Walenga, Fareed, Hoppensteadt, Emaneuele, "In vitro evaluation of heparin fractions: old vs. new methods," In: *CRC Critical Reviews in Clinical Laboratory Sciences*, 22(4):361–389, 1986.

Weeks and Davis, "Chronic intravenous cannulas for rats," *J. Appl. Physiol.*, 19:540–541, 1964.

Weiler, Freiman, Murali et al., "Serious adverse reactions to protamine sulfate: are alternatives needed?" *J. Allergy Clin. Immunol.*, 75:297–303, 1985.

Weiler, Gellhaus, Carter et al., "A prospective study of the risk of an immediate adverse reactions to protamine sulfate during cardiopulmonary bypass surgery," *J. Allergy Clin. Immunol.*, 85:713–719, 1990.

Weiss and Adkinson Jr., "NF: Allergy to protamine," *Clin. Rev. Allergy.* 9:339–355, 1991.

Yang, Bernstein, Cooney, Kadam, Langer, "Removal of the anticoagulant activities of the low molecular weight heparin fractions and fragments with flavobacterial heparinase," *Thromb. Res.*, 44:599–610, 1986.

Yang, Fu, Kim, "Protamine coated Cuprophan: a potential nonthrombogeneic hemodialysis membrane with improved biocompatibility," *ASAIO Transactions*, 37:229–232, 1991a.

Yang, Linhardt, Bernstein, Cooney, Langer, "Purification and characterization of heparinase from falvobacterium heparinum, " *J. Biol. Chem.*, 260:1849–1857, 1985.

Yang, Port, Kim, Teng, Till, Wakefield, "The use of immobilized protamine in removing heparin and preventing protamine-induced complications during extracorporeal blood circulation," *Anesthesiology*, 75:288–297, 1991b.

Yun, Ma, Fu, Yang, Meyerhoff, "Direct potentiometric membrane electrode measurements of heparin binding to macro-molecules," *Electroanalysis*, 5:719–724, 1993.

What is claimed is:

1. A purified protamine that is bioactive, that has a molecular weight of between about 400 and about 2500 Daltons and that has reduced immunoresponsiveness or toxicity compared to native protamine.

2. The protamine of claim 1, wherein said bioactive protamine is a salmine protamine.

3. The protamine of claim 1, wherein said bioactive protamine is a clupeine protamine.

4. The protamine of claim 1, wherein said bioactive protamine has a molecular weight of between about 400 and about 2000 Daltons.

5. The protamine of claim 4, wherein said bioactive protamine has a molecular weight of between about 450 and about 1500 Daltons.

6. The protamine of claim 5, wherein said bioactive protamine has a molecular weight of between about 500 and about 1350 Daltons.

7. The protamine of claim 6, wherein said bioactive protamine has a molecular weight of between about 1100 and about 1300 Daltons.

8. The protamine of claim 7, wherein said bioactive protamine has a molecular weight of about 1200 Daltons.

9. A composition comprising at least a first purified bioactive protamine in accordance with claim 1.

10. The composition of claim 9, wherein said composition comprises at least a first and at least a second purified bioactive protamine.

11. The composition of claim 10, wherein said composition comprises a plurality of purified bioactive protamines.

12. The composition of claim 9, further comprising at least one additional biologically active agent.

13. The composition of claim 12, further comprising at least one additional coagulant.

14. The composition of claim 12, further comprising at least a first therapeutic protein or polypeptide.

15. The composition of claim 14, further comprising insulin.

16. The composition of claim 15, further comprising recombinant insulin.

17. The composition of claim 15, further comprising human insulin.

18. The composition of claim 9, wherein said composition is a pharmaceutical composition.

19. The composition of claim 18, wherein said pharmaceutical composition is formulated for injection.

20. The protamine of claim 4, wherein said bioactive protamine has a molecular weight of between about 1000 and about 2000 Daltons.

21. The protamine of claim 20, wherein said bioactive protamine has a molecular weight of about 1300 Daltons.

22. The protamine of claim 20, wherein said bioactive protamine has a molecular weight of about 1400 Daltons.

23. The protamine of claim 20, wherein said bioactive protamine has a molecular weight of about 1500 Daltons.

24. The protamine of claim 20, wherein said bioactive protamine has a molecular weight of about 1600 Daltons.

25. The protamine of claim 20, wherein said bioactive protamine has a molecular weight of about 1700 Daltons.

26. The protamine of claim 20, wherein said bioactive protamine has a molecular weight of about 1800 Daltons.

27. The protamine of claim 20, wherein said bioactive protamine has a molecular weight of about 1900 Daltons.

28. The protamine of claim 20, wherein said bioactive protamine has a molecular weight of about 2000 Daltons.

29. A method of preparing at least a first bioactive protamine, that has a low molecular weight and that has reduced immunoresponsiveness or toxicity compared to native protamine, comprising contacting a native protamine composition with at least a first proteolytic composition comprising an amount of at least a first proteolytic enzyme effective to produce said at least a first bioactive protamine.

30. The method of claim 29, wherein said at least a first proteolytic composition comprises at least a first thermolysin enzyme.

31. The method of claim 29, wherein said at least a first proteolytic composition comprises at least a first ficin enzyme.

32. The method of claim 29, wherein said at least a first proteolytic composition comprises at least a first collagenase enzyme.

33. The method of claim 29, wherein said at least a first proteolytic composition comprises at least a first kallikrein enzyme.

34. The method of claim 29, wherein said at least a first proteolytic composition comprises at least a first proline-specific endopeptidase enzyme.

35. The method of claim 29, wherein said at least a first proteolytic composition comprises at least a first and at least a second proteolytic enzyme.

36. The method of claim 29, wherein said at least a first proteolytic enzyme is removed after said at least a first bioactive protamine is produced.

37. The method of claim 29, wherein at least a first and a second bioactive protamine is produced.

38. The method of claim 29, wherein a plurality of bioactive protamines are produced.

39. The method of claim 29, wherein the at least a first bioactive protamine produced has a molecular weight of between about 450 Daltons and about 1350 Daltons.

40. The method of claim 29, further comprising formulating the at least a first bioactive protamine produced in a pharmaceutically acceptable composition.

41. The method of claim 29, wherein the at least a first bioactive protamine produced has a molecular weight of between about 2000 Daltons.

42. The method of claim 41, wherein the at least a first bioactive protamine produced has a molecular weight of about 1300 Daltons.

43. The method of claim 41, wherein the at least a first bioactive protamine produced has a molecular weight of about 1400 Daltons.

44. The method of claim 41, wherein the at least a first bioactive protamine produced has a molecular weight of about 1500 Daltons.

45. The method of claim 41, wherein the at least a first bioactive protamine produced has a molecular weight of about 1600 Daltons.

46. The method of claim 41, wherein the at least a first bioactive protamine produced has a molecular weight of about 1700 Daltons.

47. The method of claim 41, wherein the at least a first bioactive protamine produced has a molecular weight of about 1800 Daltons.

48. The method of claim 41, wherein the at least a first bioactive protamine produced has a molecular weight of about 1900 Daltons.

49. The method of claim 41, wherein the at least a first bioactive protamine produced has a molecular weight of about 2000 Daltons.

50. A purified, bioactive protamine that has a molecular weight of between 400 and 2500 Daltons and that has reduced immunoresponsiveness or toxicity compared to native protamine; wherein said bioactive protamine binds to and neutralizes heparin or low molecular weight heparin, forms a complex with insulin or α-interferon or prolongs the adsorption of insulin.

51. The protamine of claim 50, wherein said bioactive protamine has a molecular weight of between 400 and 2000 Daltons.

52. The protamine of claim 51, wherein said bioactive protamine has a molecular weight of between 450 and 1500 Daltons.

53. The protamine of claim 52, wherein said bioactive protamine has a molecular weight of between 500 and 1350 Daltons.

54. The protamine of claim 53, wherein said bioactive protamine has a molecular weight of between 1100 and 1300 Daltons.

55. The protamine of claim 50, wherein said bioactive protamine has a molecular weight of between 1000 and 2000 Daltons.

56. The protamine of claim 55, wherein said bioactive protamine has a molecular weight of about 1300 Daltons.

57. The protamine of claim 55, wherein said bioactive protamine has a molecular weight of about 1400 Daltons.

58. The protamine of claim 55, wherein said bioactive protamine has a molecular weight of about 1500 Daltons.

59. The protamine of claim 55, wherein said bioactive protamine has a molecular weight of about 1600 Daltons.

60. The protamine of claim 55, wherein said bioactive protamine has a molecular weight of about 1700 Daltons.

61. The protamine of claim 55, wherein said bioactive protamine has a molecular weight of about 1800 Daltons.

62. The protamine of claim 55, wherein said bioactive protamine has a molecular weight of about 1900 Daltons.

63. The protamine of claim 55, wherein said bioactive protamine has a molecular weight of about 2000 Daltons.

64. A purified, bioactive protamine that has a molecular weight of between 400 and 2000 Daltons and that has reduced immunoresponsiveness or toxicity compared to native protamine; wherein said bioactive protamine binds to and neutralizes heparin or low molecular weight heparin or prolongs the adsorption of insulin.

65. A purified, bioactive protamine that has a molecular weight of between 400 and 2000 Daltons, that retains heparin binding and neutralization activity and that has reduced immunoresponsiveness or toxicity compared to native protamine.

66. The protamine of claim 65, wherein said bioactive protamine has a molecular weight of between 450 and 1500 Daltons.

67. The protamine of claim 66, wherein said bioactive protamine has a molecular weight of between 500 and about 1350 Daltons.

68. The protamine of claim 67, wherein said bioactive protamine has a molecular weight of between 1100 and 1300 Daltons.

69. The protamine of claim 65, wherein said bioactive protamine has a molecular weight of between 1000 and 2000 Daltons.

70. The protamine of claim 69, wherein said bioactive protamine has a molecular weight of about 1300 Daltons.

71. The protamine of claim 69, wherein said bioactive protamine has a molecular weight of about 1400 Daltons.

72. The protamine of claim 69, wherein said bioactive protamine has a molecular weight of about 1500 Daltons.

73. The protamine of claim 69, wherein said bioactive protamine has a molecular weight of about 1600 Daltons.

74. The protamine of claim 69, wherein said bioactive protamine has a molecular weight of about 1700 Daltons.

75. The protamine of claim 69, wherein said bioactive protamine has a molecular weight of about 1800 Daltons.

76. The protamine of claim 69, wherein said bioactive protamine has a molecular weight of about 1900 Daltons.

77. The protamine of claim 69, wherein said bioactive protamine has a molecular weight of about 2000 Daltons.

78. A kit comprising at least a first container that comprises at least a first purified bioactive protamine in accordance with claim 1.

79. The kit of claim 78, further comprising at least one additional anticoagulant.

80. The kit of claim 79, wherein said at least one anticoagulant is heparin or low molecular weight heparin.

81. A purified, bioactive protamine that has a molecular weight of between 1000 and 2000 Daltons, that retains heparin binding and neutralization activity and that has reduced immunoresponsiveness or toxicity compared to native protamine.

82. The protamine of claim 81, wherein said bioactive protamine has a molecular weight of about 1300 Daltons.

83. The protamine of claim 81, wherein said bioactive protamine has a molecular weight of about 1400 Daltons.

84. The protamine of claim 81, wherein said bioactive protamine has a molecular weight of about 1500 Daltons.

85. The protamine of claim 81, wherein said bioactive protamine has a molecular weight of about 1600 Daltons.

86. The protamine of claim 81, wherein said bioactive protamine has a molecular weight of about 1700 Daltons.

87. The protamine of claim 81, wherein said bioactive protamine has a molecular weight of about 1800 Daltons.

88. The protamine of claim 81, wherein said bioactive protamine has a molecular weight of about 1900 Daltons.

89. The protamine of claim 81, wherein said bioactive protamine has a molecular weight of about 2000 Daltons.

* * * * *

UNITED STATES PATENT AND TRADEMARK OFFICE
CERTIFICATE OF CORRECTION

PATENT NO. : 6,624,141 B1  Page 1 of 1
DATED : September 23, 2003
INVENTOR(S) : Yang et al.

It is certified that error appears in the above-identified patent and that said Letters Patent is hereby corrected as shown below:

Title page,
Item [22], PCT Filed, delete "Mar. 9, 1999" and insert -- Mar. 15, 2000 --
Item [56], References Cited, U.S. PATENT DOCUMENTS, after "530/304", please insert -- * --.
FOREIGN PATENT DOCUMENTS, after "WO 96 35444", please insert -- * --.
OTHER PUBLICATIONS, after the reference "Ando and Watanabe, "A New Method for Fractionation of Protamines and the Amino Acid Sequences of Salmine and Three Components of Iridine," *Int. J. Protein Research I*, 221-224, 1969.", please insert -- * --.

Column 47,
Line 67, delete "between about 2000 Daltons" and insert -- between about 1000 and about 2000 Daltons --.

Signed and Sealed this

Seventeenth Day of February, 2004

JON W. DUDAS
*Acting Director of the United States Patent and Trademark Office*